US012496300B2

(12) United States Patent
Snyder et al.

(10) Patent No.: US 12,496,300 B2
(45) Date of Patent: *Dec. 16, 2025

(54) METHODS OF TREATING ACUTE DEPRESSION AND ANXIETY

(71) Applicant: INTRA-CELLULAR THERAPIES, INC., Bedminster, NJ (US)

(72) Inventors: Gretchen Snyder, New York, NY (US); Robert Davis, San Diego, CA (US); Lawrence P. Wennogle, Steamboat Springs, CO (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/005,181

(22) Filed: Dec. 30, 2024

(65) Prior Publication Data

US 2025/0127779 A1 Apr. 24, 2025

Related U.S. Application Data

(63) Continuation of application No. 18/621,067, filed on Mar. 28, 2024, which is a continuation of application No. 16/981,639, filed as application No. PCT/US2019/022480 on Mar. 15, 2019, now Pat. No. 11,980,617.

(60) Provisional application No. 62/780,004, filed on Dec. 14, 2018, provisional application No. 62/682,582, filed on Jun. 8, 2018, provisional application No. 62/644,355, filed on Mar. 16, 2018.

(51) Int. Cl.

| | |
|---|---|
| *A61K 31/4985* | (2006.01) |
| *A61K 9/00* | (2006.01) |
| *A61K 31/13* | (2006.01) |
| *A61K 31/135* | (2006.01) |
| *A61K 31/137* | (2006.01) |
| *A61K 31/138* | (2006.01) |
| *A61K 31/155* | (2006.01) |
| *A61K 31/165* | (2006.01) |
| *A61K 31/197* | (2006.01) |
| *A61K 31/343* | (2006.01) |
| *A61K 31/36* | (2006.01) |
| *A61K 31/38* | (2006.01) |
| *A61K 31/381* | (2006.01) |
| *A61K 31/42* | (2006.01) |
| *A61K 31/485* | (2006.01) |
| *A61K 31/55* | (2006.01) |
| *A61K 31/5513* | (2006.01) |
| *A61K 38/07* | (2006.01) |
| *A61P 25/24* | (2006.01) |

(52) U.S. Cl.

CPC .......... *A61K 31/4985* (2013.01); *A61K 9/006* (2013.01); *A61K 31/13* (2013.01); *A61K 31/135* (2013.01); *A61K 31/137* (2013.01); *A61K 31/138* (2013.01); *A61K 31/155* (2013.01); *A61K 31/165* (2013.01); *A61K 31/197* (2013.01); *A61K 31/343* (2013.01); *A61K 31/36* (2013.01); *A61K 31/38* (2013.01); *A61K 31/381* (2013.01); *A61K 31/42* (2013.01); *A61K 31/485* (2013.01); *A61K 31/55* (2013.01); *A61K 31/5513* (2013.01); *A61K 38/07* (2013.01); *A61P 25/24* (2018.01)

(58) Field of Classification Search

CPC .................................................. A61K 31/4985

See application file for complete search history.

(56) References Cited

U.S. PATENT DOCUMENTS

| | | | |
|---|---|---|---|
| 4,136,145 | A | 1/1979 | Fuchs et al. |
| 4,238,607 | A | 12/1980 | Rajagopalan |
| 4,389,330 | A | 6/1983 | Tice et al. |
| 4,530,840 | A | 7/1985 | Tice et al. |
| 5,004,602 | A | 4/1991 | Hutchinson |
| 5,114,976 | A | 5/1992 | Norden |
| 5,151,419 | A | 9/1992 | Perenyi et al. |
| 5,538,739 | A | 7/1996 | Bodmer et al. |
| 5,629,003 | A | 5/1997 | Horstmann et al. |
| 5,763,476 | A | 6/1998 | Delbressine et al. |
| 5,922,338 | A | 7/1999 | Brich et al. |
| 5,948,430 | A | 9/1999 | Zerbe et al. |
| 6,544,599 | B1 | 4/2003 | Mesens et al. |
| 6,548,493 | B1 | 4/2003 | Robichaud et al. |
| 6,552,017 | B1 | 4/2003 | Robichaud et al. |
| 6,552,024 | B1 | 4/2003 | Chen et al. |

(Continued)

FOREIGN PATENT DOCUMENTS

| | | | |
|---|---|---|---|
| WO | 2015/085004 | | 6/2015 |
| WO | 2017/120012 | A1 | 7/2017 |
| WO | WO-2017117514 | A1 * | 7/2017 |

OTHER PUBLICATIONS

Intra-Cellular Therapies, Inc., "Corporate Presentation," (Sep. 24, 2019), downloaded from https://ir.intracellulartherapies.com/static-files/93b08960-f01c-4864-aa22-8cadb3539753 (last accessed Mar. 13, 2023).

(Continued)

*Primary Examiner* — James D. Anderson

(74) *Attorney, Agent, or Firm* — Hoxie & Associates LLC

(57) ABSTRACT

The disclosure provides methods for the acute treatment of depression and/or anxiety, for the enhancement of mTOR (e.g., mTORC1) signaling, and for the reduction of neuroinflammation, comprising administering to a patient in need thereof, a therapeutically effective amount of a 5-HT2A or 5-HT2A/D2 receptor ligand, e.g. lumateperone.

27 Claims, 10 Drawing Sheets

(56) References Cited

U.S. PATENT DOCUMENTS 6,699,852 B2 3/2004 Robichaud et al.
6,713,471 B1 3/2004 Robichaud et al.
6,849,619 B2 2/2005 Robichaud et al.
6,929,803 B2 8/2005 Wong et al.
7,071,186 B2 7/2006 Robichaud et al.
7,081,455 B2 7/2006 Robichaud et al.
7,183,282 B2 2/2007 Robichaud et al.
RE39,679 E 6/2007 Robichaud et al.
RE39,680 E 6/2007 Robichaud et al.
7,238,690 B2 7/2007 Robichaud et al.
7,601,740 B2 10/2009 Weiner et al.
7,645,752 B2 1/2010 McDevitt et al.
7,998,971 B2 8/2011 Barlow et al.
8,309,722 B2 11/2012 Tomesch et al.
8,414,922 B2 4/2013 Bryson et al.
8,598,119 B2 12/2013 Mates et al.
8,648,077 B2 2/2014 Tomesch et al.
8,652,378 B1 2/2014 Yang et al.
8,779,139 B2 7/2014 Seeman et al.
8,791,138 B2 7/2014 Seeman et al.
8,835,459 B2 9/2014 Kottayil et al.
8,900,497 B2 12/2014 Yang et al.
8,900,498 B2 12/2014 Yang et al.
8,906,277 B2 12/2014 Yang et al.
8,993,572 B2 3/2015 Mates et al.
9,108,340 B2 8/2015 Yang et al.
9,168,258 B2 10/2015 Mates et al.
9,199,995 B2 12/2015 Tomesch et al.
9,216,175 B2 12/2015 Amancha et al.
9,315,504 B2 4/2016 Tomesch et al.
9,371,324 B2 6/2016 Mates et al.
9,393,192 B2 7/2016 Yam et al.
9,427,412 B2 8/2016 Bryson et al.
9,428,506 B2 8/2016 Mates et al.
9,586,960 B2 3/2017 Tomesch et al.
9,616,061 B2 4/2017 Mates et al.
9,708,322 B2 7/2017 Li et al.
9,745,300 B2 8/2017 Mates et al.
9,751,883 B2 9/2017 Tomesch et al.
9,956,227 B2 5/2018 Vanover et al.
10,072,010 B2 9/2018 Li et al.
10,077,267 B2 9/2018 Mates et al.
10,117,867 B2 11/2018 Mates et al.
10,118,926 B2 11/2018 Koolman et al.
10,245,260 B2 4/2019 Yao et al.
10,322,134 B2 6/2019 Vanover et al.
10,464,938 B2 11/2019 Tomesch et al.
10,472,359 B2 11/2019 Li et al.
10,597,394 B2 3/2020 Mates et al.
10,654,854 B2 5/2020 Li et al.
10,682,354 B2 6/2020 Wennogle et al.
10,688,097 B2 6/2020 Yao et al.
10,695,345 B2 6/2020 Li et al.
10,702,522 B2 7/2020 Mates et al.
10,716,786 B2 7/2020 Li et al.
10,799,500 B2 10/2020 Yao et al.
10,844,061 B2 11/2020 Li et al.
10,899,762 B2 1/2021 Mates et al.
10,960,009 B2 3/2021 Vanover et al.
10,960,010 B2 3/2021 Vanover et al.
11,026,951 B2 6/2021 Mates et al.
11,052,083 B2 7/2021 Li et al.
11,052,084 B2 7/2021 Li et al.
11,053,245 B2 7/2021 Mates et al.
11,096,944 B2 8/2021 Yao et al.
11,124,514 B2 9/2021 Mates et al.
RE48,825 E 11/2021 Tomesch et al.
RE48,839 E 12/2021 Mates et al.
11,311,536 B2 4/2022 Li et al.
11,331,316 B2 5/2022 Li et al.
11,376,249 B2 7/2022 Li et al.
11,407,751 B2 8/2022 Tomesch et al.
11,427,587 B2 8/2022 Li et al.
11,440,911 B2 9/2022 Wennogle et al.
11,560,382 B2 1/2023 Mates et al.
11,680,065 B2 6/2023 Li et al.
11,690,842 B2 7/2023 Li et al.
11,723,909 B2 8/2023 Yao et al.
11,753,419 B2 9/2023 Li et al.
11,806,347 B2 11/2023 Li et al.
11,806,348 B2 11/2023 Li et al.
11,957,791 B2 4/2024 Li et al.
11,958,852 B2 4/2024 Mates et al.
11,980,617 B2 * 5/2024 Snyder ................. A61K 31/155
12,023,331 B2 7/2024 Snyder et al.
12,070,459 B2 8/2024 Li et al.
12,090,155 B2 9/2024 Mates et al.
12,128,043 B2 10/2024 Li et al.
12,144,808 B2 11/2024 Li et al.
12,194,044 B2 1/2025 Yao et al.
2008/0287450 A1 11/2008 Cid-Nunez et al.
2011/0071080 A1 3/2011 Mates et al.
2011/0269777 A1 11/2011 Bachurin et al.
2015/0374684 A1 12/2015 Javitt et al.
2016/0031885 A1 2/2016 Li et al.
2016/0310502 A1 10/2016 Vanover et al.
2019/0192511 A1 6/2019 Li et al.
2019/0211015 A1 7/2019 Mittleman et al.
2020/0148683 A1 5/2020 Peddy et al.
2020/0157100 A1 5/2020 Li
2020/0392135 A1 12/2020 Wennogle et al.
2021/0008065 A1 1/2021 Li et al.
2021/0009592 A1 1/2021 Li et al.
2021/0070755 A1 3/2021 Berecz et al.
2021/0186962 A1 6/2021 Davis et al.
2023/0312573 A1 10/2023 Li et al.
2023/0372336 A1 11/2023 Dutheil et al.

OTHER PUBLICATIONS

Aiken, C., "An Overview of Atypical Antipsychotics for Bipolar Depression," published on Jan. 3, 2020 at https://www.psychiatrictimes.com/view/overview-atypical-antipsychotics-bipolar-depression, 11 pages.

Angst et al. "Prevalence and Characteristics of Undiagnosed Bipolar Disorders in Patients With a Major Depressive Episode", Arch Gen Psychiatry, vol. 68(8), p. 701-709, (2011).

Bobo et al., "Fluoxetine and Olanzapine Combination Therapy in Treatment-resistant Major Depression: Review of Efficacy and Safety Data," Expert Opinion on Pharmacotherapy, vol. 10, No. 13, p. 2145-2159, (2009).

Bryan-Lluka et al., "Potencies of Haloperidol Metabolites as Inhibitors of the Human Noradrenaline, Dopamine and Serotonin Transporters in Transfected COS-7 Cells," Naunyn-Shemiedeberg's Arch Pharmacol, vol. 360, pp. 109-115, (1999).

Calabrese et al., "Efficacy and Safety of Lumateperone for Major Depressive Episodes Associated with Bipolar I or Bipolar II Disorder: A Phase 3 Randomized Placebo-Controlled Trial," American Journal of Psychiatry, vol. 178, No. 12, p. 1098-1106, (2021), published online Sep. 23, 2021, <<https://doi.org/10.1176/appi.aip.2021.20091339>>.

"Clinical Trial Evaluating ITI-007 (Lumateperone) as a Monotherapy for the Treatment of Bipolar," ClinicalTrials.gov (Identifier: NCT02600494), 5 pages, (2015).

Coyle et al., Dialogues Clin Neurosci., vol. 12, No. 3, p. 359-382, (2010).

Darmani, et al., "Do Functional Relationships Exist Between 5-$HT_{1A}$ and 5-$HT_2$ Receptors?" *Pharmacology and Biochemistry & Behavior*, vol. 36, pp. 901-906, (1990).

Davis, et al., "ITI-007 in the Treatment of Schizophrenia: From Novel Pharmacology to Clinical Outcomes," *Expert Review of Neurotherapeutics*, vol. 16, No. 6, pp. 601-614, (2016).

Davis et al., "ITI-007: A Novel Treatment for Behavioral Disturbances Associated with Dementia and Related Disorders," Clinical Trials in Alzheimer's Disease (CTAD) Congress 2014 (2014) (poster presentation).

Davis et al., "Rationale for the Development of Low Doses of ITI-007 for the Treatment of Behavioral Disturbances Associated with Dementia," The Journal of Prevention of Alzheimer's Disease, 2(4):302 (2015) (Clinical Trials in Alzheimer's Disease (CTAD)

(56) References Cited

OTHER PUBLICATIONS

Congress, Symposium Summary OC51).
Davis, et al., "ITI-007 demonstrates brain occupancy at serotonin 5-HT2A and dopamine D2 receptors and serotonin transporters using positron emission tomography in healthy volunteers," Psychopharmacology, vol. 232, pp. 2863-2872, (2015); DOI: 10.1007/s00213-015-3922-1.
Davis, et al., "Lumateperone (ITI-007), A Novel Drug in Development for the Treatment of Agitation in Patients with Dementia, including Alzheimer's Disease: Rationale and Clinical Design," The Journal of Prevention of Alzheimer's Disease, 4(4):372 (2017) (Clinical Trials in Alzheimer's Disease (CTAD) Congress, Symposium Summary P93.
Del-Monte et al., Psychiatry Res., vol. 210, p. 29-35, (2013).
Docherty et al., Schizophrenia Res., vol. 120, p. 199-203, (2010).
Gramigna, J, "Lumateperone Safe, Effective for Depressive Symptoms Among Patients with Bipolar Disorders," American Society of Clinical Psychopharmacology Annual Meeting, Jun. 2, 2020, 3 pages.
Harvey, et al., "Lumateperone Improves Negative Symptoms Related to Emotional Experience (Avolition) in Patient with Schizophrenia," Abstract presented at the American Society of Clinical Psychopharmacology (ASCP) Annual Meeting; May 29-Jun. 1, 2018; Miami, FL.
Helfer et al., Am J Psychiatry, vol. 173, No. 9, p. 876-886, (2016).
Hlavinka, E., "Schizophrenia Tx Eases Depression in Bipolar Disorder: Lumateperone Offers Greater Rate of Response, Remission versus Placebo," Medpage Today, 7 pages, (2020); https://www.medpagetoday.com/meetingcoverage/psychcongress/88584.
Howes et al., J Psychopharmacol., vol. 29, No. 2, p. 97-115, (2015).
Kantrowitz, J.T., "The Potential Role of Lumateperone—Something Borrowed? Something New?," JAMA Psychiatry, vol. 77, No. 4, p. 343-344, (2020); Abstract Only.
Khorana, et al., "Gamma-Carbolines: Binding at 5-HT5A Serotonin Receptors," *Bioorganic & Medicinal Chemistry*, vol. 11, pp. 717-722, p. 718 Table 1, (2003).
Kumar et al., "Lumateperone: A New Treatment Approach for Neuropsychiatric Disorders," Drugs of Today, vol. 54, No. 12, p. 713-719, (2018).
Lammers, et al., "Risperidone Long-acting Injection in Schizophrenia Spectrum Illnesses Compared to First Generation Depot Antipsychotics in an Outpatient Setting in Canada," BMC Psychiatry, vol. 13, No. 155, 9 pages, (2013); http://www.biomedcentral.com/1471-244X/13/155.
Lee, et al. "Novel, Highly Potent, Selective 5-$HT_{2A}/D_2$ Receptor Antagonists as Potential Atypical Antipsychotics," *Bioorg. Med. Chem. Lett.*, vol. 13, pp. 767-770, (2003).
Li, et al., "Discovery of a Tetracyclic Quinoxaline Derivative as a Potent and Orally Active Multifunctional Drug Candidate for the Treatment of Neuropsychiatric and Neurological Disorders," *Journal of Medicinal Chemistry*, vol. 57, pp. 2670-2682, (2014).
Lieberman, J.A., et al., "ITI-007 for the Treatment of Schizophrenia: A 4-Week Randomized, Double-Blind, Controlled Trial," Biol. Psychiatry, vol. 79, No. 12, pp. 952-961, (2015).
Liebermann et al., "ITI-007 for the Treatment of Schizophrenia: A 4-Week Randomized, Double-Blind, Controlled Trial," Biological Psychiatry, vol. 79, p. 952-961, (2016).
Lindstrom et al., Nord J Psychiatry, vol. 47, No. 4, p. 257-263, (1993).
Makadia et al., "Poly Lactic-co-Glycolic Acid (PLGA) as Biodegradable Controlled Drug Delivery Carrier," Polymers (Basel), vol. 3, No. 3, pp. 1377-1397, (2011).
Marek et al. Synergistic Action of 5-HT2A Antagonists and Selective Serotonin Reuptake Inhibitors in Neuropsychiatric Disorders. Neuropsychopharmacology, 2003. Vol. 28, pp. 402-412. (Year: 2003).
Mass et al., Schizophrenia Bull., vol. 26, No. 1, p. 167-177, (2000).
McIntyre et al., "Rapid-acting Antidepressants in Psychiatry: Psychedelics, Episodic Treatments, Innovation, and Clarion Call for Methodologic Rigor in Drug Development," Expert Opinion on Drug Safety, vol. 21, No. 6, p. 715-716, (2022).
Medisorb Fact Sheet in Medisorb Microspheres Technology (Jan. 2009) at https://static.secure.website/wscfus/6472891/uploads/Medisorb.pdf (retrieved from the internet May 18, 2020) (Year: 2009).
Menard, et al., "Social stress induces neurovascular pathology promoting depression," Nature Neuroscience 20:1752-60 (2017).
Möller and P Czobor, Eur Arch Psychiatry Clin Neurosci., vol. 265, p. 567-578, (2015).
Mueller et al., "Detection of Depression in Acute Schizophrenia: Sensitivity and Specificity of 2 Standard Observer Rating Scales," Can J Psychiatry, vol. 51, No. 6, pp. 387-392, (2006).
O'Gorman et al., "Lumateperone (ITI-007): A Novel Investigational Agent with Broad Therapeutic Potential Across Multiple Neuropsychiatric Disorders," Poster P.1.g.038, European College of Neuropsychopharmacology (ECNP) Congress (2017).
Palanisamy, M. et al., "Cellulose-Based Matrix Microspheres of Prednisolone Inclusion Complex; Preparation and Characterization." American Association of Pharmaceutical Scientists PharmSciTech, vol. 12, No. 1, pp. 388-400, (2011).
Perlis et al., "Clinical Features of Bipolar Depression Versus Major Depressive Disorder in Large Multicenter Trials", Am J Psychiatry, vol. 163, p. 225- 231, (2006).
Press Release, "Intra-Cellular Therapies Announces Additional Results from Phase I/II Clinical Trail for ITI-007 in Healthy Geriatric Subjects and Patients With Dementia," Intra-Cellular Therapies, Press Release Date: Nov. 21, 2014, (http://ir.intracellulartherapies.com/releasedetail.cfm?ReleaseID=884325), accessed on May 31, 2016.
Press Release, "Intra-Cellular Therapies Presents Data on Symptom Improvement by Lumateperone on Negative Symptoms, Depression, and Social Function in Patients with Schizophrenia at the American Society of Clinical Psychopharmacology (ASCP) Annual Meeting," Intra-Cellular Therapies, Press Release Date: May 31, 2018, (https://ir.intracellulartherapies.com/newsreleases/.
Press Release, "Intra-Cellular Therapies Announces Positive Top-Line Results from a Phase 3 Trial of Lumateperone in Patient with Bipolar Depression," Intra-Cellular Therapies, Press Release Date: Jul. 8, 2019.
Puig et al., "Serotonin and Prefrontal Cortex Function: Neurons, Networks, and Circuits," Mol. Neurobiol., 44(3):449-464 (2011).
Rainer, M.K., "Risperidone Long-acting Injection: A Review of its Long Term Safety and Efficacy," *Neuropsychiatric Disease and Treatment*, vol. 4, No. 5, pp. 919-927, (2008).
Rummel et al., Schizophrenia Res., vol. 80, p. 85-97, (2007).
Satlin, et al., "ITI-007 (Lumateperone) for the Treatment of Agitation in Patients with Dementia, including Alzheimer's Disease," Poster P2-032, Alzheimer's Assoc. International Conference 2018 (2018).
Satlin, et al., "ITI-007 (Lumateperone) for the Treatment of Agitation in Patients with Dementia, including Alzheimer's Disease," Alzheimer's & Dementia 14(7) (Suppl.): P678-79 (2018) (Alzheimer's Assoc. International Conference 2018, summary of Poster P2-032).
Sepehry et al., J Clin Psychiatry, vol. 68, No. 4, p. 604-610, (2007).
Silver et al., Neurotherapeutics, vol. 6, p. 86-93, (2009).
Singh et al., The British Journal of Psychiatry, vol. 197, p. 174-179, (2010).
Snyder, et al., "Functional Profile of a Novel Modulator of Serotonin, Dopamine, and Glutamate Neurotransmission," *Psychopharmacology*, vol. 232, pp. 605-621, (2015); Published online Aug. 2014, DOI 10.1007/s00213-014-3704-1.
Tohen, M., et al., "Efficacy of Olanzapine and Olanzapine-Fluoxetine Combination in the Treatment of Bipolar I Depression," Arch Gen Psychiatry, vol. 60, pp. 1079-1088, (2003).
Vanover et al., Abstracts of the 13th International Congress on Schizophrenia (ICOSR) (Apr. 2-6, 2011), Schizophrenia Bull., 37 Suppl. 1, p. 325, (Mar. 2011).
Vanover, et al., "Dopamine D2 receptor occupancy of lumateperone (ITI-007): a Positron Emission Tomography Study in patients with schizophrenia," *Neuropsychopharmacology* 44:598-605, (2019).

(56) References Cited

OTHER PUBLICATIONS

Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.

Vanover, K., et al., "ITI-007: A Novel Therapy for the Treatment of Schizophrenia and Related Psychoses," International Clinical Psychopharamcology, vol. 26, e56, 1 page, (2011).

Vyas, P., et al., "An Evaluation of Lumateperone Tosylate for the Treatment of Schizophrenia," Expert Opinion on Pharmacotherapy, vol. 21, No. 2, pp. 139-145, (2020); https://doi.org/10.1080/14656566.2019.1695778.

Wang et al., "Rapid-acting Antidepressants Targeting Modulation of the Glutamatergic System: Clinical and Preclinical Evidence and Mechanisms," General Psychiatry, vol. 35, No. e100922, 6 pages (2022).

Wennogle, et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.

Zhang et al., "The In Vivo Effects of Olanzapine and Other Antipsychotic Agents on Receptor Occupancy and Antagonism of Dopamine $D_1$, $D_2$, $D_3$, $5HT_{2A}$ and Muscarinic Receptors," Psychopharmacology, vol. 141, p. 267-278, (1999).

"ACNP 58th Annual Meeting: Poster Session II: Abstracts Collection" Neuropsychopharmacology, vol. 44, p. 230-384, (2019); 3 parts.

"Clinical Trial Evaluating ITI-007 as an Adjunctive Therapy to Lithium or Valproate for the Treatment of Bipolar Depression," ClinicalTrials.gov, 6 pages, Nov. 9, 2015.

Barman, R. et al., "Newer Antipsychotics: Brexpiprazole, Cariprazine, and Lumateperone: A Pledge or Another Unkept Promise?," World J. Psychiatr., vol. 11, No. 12, pp. 1228-1238, (2021).

Correll, C. et al., "Efficacy and Safety of Lumateperone for Treatment of Schizophrenia A Randomized Clinical Trial," JAMA Psychiatry, vol. 77, No. 4, pp. 349-358, (2020).

Dutheil, S., et al. "Lumateperone Normalizes Pathological Levels of Acute Inflammation through Important Pathways Known to Be Involved in Mood Regulation," The Journal of Neuroscience, vol. 43, No. 5, pp. 863-877, (2023).

Galea, I., "The Blood-Brain Barrier in Systemic Infection and Inflammation," Cellular & Molecular Immunology, vol. 18, p. 2489-2501, (2021).

Mazza, M. et al., "Evidence on the New Drug Lumateperone (ITI-007) for Psychiatric and Neurological Disorders," CNS & Neurological Disorders—Drug Targets, vol. 19, pp. 243-247, (2020).

Snyder, G. et al., "Chapter 11: A review of the pharmacology and clinical profile of lumateperone for the treatment of schiophrenia," Advances in Pharmacology, vol. 90, pp. 253-276, 31 pages, (2021).

Suppes, T. et al., "Adjunctive lumateperone (ITI-007) in the treatment of bipolar depression: Results from a randomized placebo-controlled clinical trial," Bipolar Disorders, vol. 25, pp. 478-488, 11 pages, (2023).

Vanover, K. et al., "50. ITI-007, an Investigational New Antipsychotic Drug with a Novel Pharmacological Profile, is Safe and Well-Tolerated with Early Clinical Signs for Efficacy in Patients with Stabilized Schizophrenia," Abstract presented at the ANCP 49th Annual Conference in Poster Session III; Dec. 8, 2010; pp. S321-S322; Neuropsychopharmacology, vol. 35, (2010).

Vanover, K. et al., "Safety, Pharmacokinetics and Early Signals for Efficacy with ITI-007, A Novel Investigational New Drug for the Treatment of Schizophrenia and Related Disorders," Schizophrenia Bulletin, vol. 37, Suppl. 1, p. 325, (2011), Abstract only.

Warner-Schmidt, J. et al., "Antidepressant Effects of Selective Serotonin Reuptake Inhibitors (SSRIs) are Attenuated by Antiinflammatory Drugs in Mice and Humans," PNAS, vol. 108, No. 22, pp. 9262-9267, (2011).

Witkin, J. et al., "Chapter 3: Rapid-acting Antidepressants," Advances in Pharmacology, vol. 86, 50 pages, (2019).

"Highlights of Prescribing Information CAPLYTA (lumateperone) capsules, for oral use," Label—Prescribing Information, 16 pages, (2019); https://www.accessdata.fda.gov/drugsatfda_docs/label/2019/209500s000lbl.pdf.

"Clinical Practice Guideline—Management of Bipolar Disorder in Adults", Department of Veterans Affairs and the Department of Defense, 176 pages, (2010).

"Rating Scales and Safety Measurements in Bipolar Disorder and Schizophrenia—A Reference Guide," Psychopharmacol. Bull., vol. 47, No. 3, p. 77-109 (2017).

Altschuler et al., "Lower Switch Rate in Depressed Patients with Bipolar II than Bipolar I Disorder Treated Adjunctively with Second-Generation Antidepressants," Am. J. Psychiatry, vol. 163, No. 2, p. 313-315 (2006).

Bastin, R. et al., "Salt Selection and Optimized Procedures for Pharmaceutical New Chemical Entities," Organic Process and Research Development, vol. 4, No. 5, pp. 427-435, (2000).

Cascade et al., "Antidepressants in Bipolar Disorder," Psychiatry (Edgmont), vol. 4, No. 3, p. 56-58 (2007).

Celada et al., "The Therapeutic Role of 5-HT1A and 5-HT2A Receptors in Depression," Rev. Psychiatr. Neurosci., vol. 29, No. 4, p. 252-265 (2004).

Citrome et al., "Toward Convergence in the Medication Treatment of Bipolar Disorder and Schizophrenia," Harv. Rev. Psychiatry, vol. 13, No. 1, p. 28-42 (2005).

Defendants' Joint Initial Invalidity Contentions, Ex. M ('617 Patent), Intra-Cellular Therapies Inc., v. Aurobindo Pharma. Ltd., C.A. No. 3:24-cv-04264-MAS-JBD (U.S. Dist. Ct., D. N.J.) (filed Jan. 28, 2025).

Ghaemi, N., "Expert Commentary—Antidepressants in Bipolar Disorder," Psychiatry (Edgmont), vol. 4, No. 3, p. 56-58 (2007).

Gould, P., "Salt selection for basic drugs," Int'l J. Of Pharms., vol. 33, p. 201-217 (1986).

Intra-Cellular Press Release, "Intra-Cellular Therapies Presents Data on Lumateperone, ITI-214 and ITI-333 at the 56th Annual Meeting of the American College of Neuropsychopharmacology" (Dec. 7, 2017).

Intra-Cellular Press Release, "Intra-Cellular Therapies Reports Initiation of Patient Enrollment for ITI-007 Phase I Clinical Trials in Bipolar Depression", (Dec. 23, 2015).

Montgomery et al., "Pharmacotherapy of Depression and Mixed States in Bipolar Disorder," J. Affect. Disord., vol. 59, p. S39-S56 (2000).

Mortimer, "Symptom Rating Scales and Outcome in schizophrenia," Brit. J. Psychiatry, vol. 191, Suppl. No. 50, p. s7-s14 (2007).

Press Release, "Intra-Cellular Therapies, Inc. Receives Exclusive License for Central Nervous System Compounds from Bristol-Myers Squibb Company," Intra-Cellular Therapies, Inc. Press Release Date: Jun. 1, 2005.

Shah, et al., "Clinical Practice Guidelines for Management of Bipolar Disorder," Indian J. Psychiatry, 59:51-66 (2017).

Yatham, L.N., "A clinical review of aripiprazole in bipolar depression and maintenance therapy of bipolar disorder," J. Affect. Disord., vol. 128, Suppl 1: s21-8, (2011).

Yatham, L.N., "Atypical Antipsychotics for Bipolar Disorder," Psychiatr. Clin. N. Am., vol. 28, No. 2, p. 325-347 (2005).

* cited by examiner

| Compound | SERT Ki (nM) |
|---|---|
| Lumateperone | 26-62 |
| IC200131 | 70 |
| Risperidone | >1000 |
| Olanzapine | >1000 |
| Aripiprazole | 98 |
| Lurasidone | >1000 |
| Clozapine | 1624 |
| Quetiapine | 3676 |
| Haldol | 3256 |

FIG. 3 p < 0.05,  p < 0.01, * p < 0.001, ** p < 0.0001 (compared to saline/vehicle control)*

METHODS OF TREATING ACUTE DEPRESSION AND ANXIETY

CROSS REFERENCE TO RELATED APPLICATIONS

This application is a continuation of U.S. application Ser. No. 18/621,067, filed on Mar. 28, 2024, which is a continuation of U.S. application Ser. No. 16/981,639, filed on Sep. 16, 2020, which is a United States Application under 35 U.S.C. § 371 claiming priority to and the benefit of International Application No. PCT/US2019/022480, filed on Mar. 15, 2019, which claims priority to and the benefit of U.S. Provisional Application No. 62/780,004, filed on Dec. 14, 2018, 62/682,582, filed on Jun. 8, 2018, and 62/644,355, filed on Mar. 16, 2018, the contents of each of which are hereby incorporated by reference in their entireties.

TECHNICAL FIELD

The present disclosure relates to use of a 5-$HT_{2A}$ or 5-$HT_{2A}$/D2 receptor ligand, for example a substituted heterocycle fused gamma-carbolines as described herein, in free, pharmaceutically acceptable salt or prodrug form, for acute treatment of depression and anxiety.

BACKGROUND OF THE INVENTION

Substituted heterocycle fused gamma-carbolines such as lumateperone are known to be 5-$HT_{2A}$ or 5-$HT_{2A}$/D2 receptor ligands, which are useful in treating central nervous system disorders. These compounds antagonize the serotonin-2A (5-$HT_{2A}$) receptor, and/or modulate dopamine receptor signaling at the level of key intra-cellular phosphoproteins. Such compounds are principally known to be useful for the treatment of positive and negative symptoms of schizophrenia. At dopamine D2 receptors, these compounds have dual properties and act as both post-synaptic antagonists and pre-synaptic partial agonists. They also stimulate phosphorylation of glutamatergic NMDA NR2B, or GluN2B, receptors in a mesolimbic specific manner. It is believed that this regional selectivity in the brain areas thought to mediate the efficacy of antipsychotic drugs, together with the serotonergic, glutamatergic, and dopaminergic interactions, may result in antipsychotic efficacy for positive, negative, affective and cognitive symptoms associated with schizophrenia. The compounds also exhibit serotonin reuptake inhibition, providing antidepressant activity for the treatment of schizoaffective disorder, co-morbid depression, and/or as a stand-alone treatment for major depressive disorder. The 5-$HT_{2A}$ or 5-$HT_{2A}$/D2 receptor ligands as described are also useful for the treatment of bipolar disorder and other psychiatric and neurodegenerative disorders, particularly behavioral disturbances associated with dementia, autism and other CNS diseases. These features may be able to improve the quality of life of patients with schizophrenia and enhance social function to allow them to more fully integrate into their families and their workplace. These compounds display differential dose-dependent effects, selectively targeting the 5-$HT_{2A}$ receptor at low doses, while progressively interacting with the D2 receptor at higher doses. As a result, at lower doses, they are useful in treating sleep, aggression and agitation. At a high-dose, they can treat acute exacerbated and residual schizophrenia, bipolar disorders, and mood disorders.

Lumateperone, having the formula:

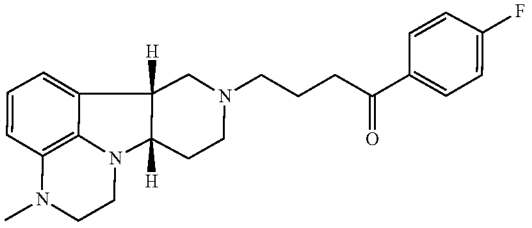 [SMILES: CN1CCN2c3c(cccc31)[C@@H]1CN(CCCC(=O)c3ccc(F)cc3)CC[C@@H]12]

is a novel therapeutic agent with potent (Ki=0.5 nM) 5-$HT_{2A}$ receptor antagonism, activity as a mesolimbic/mesocortical-selective dopamine receptor protein phosphorylation modulator consistent with presynaptic D2 receptor partial agonism and postsynaptic D2 receptor antagonism (Ki=32 nM) in vivo, high D1 receptor affinity (Ki=52 nM), and inhibition of the serotonin transporter (SERT) (Ki=26-62 nM, using different assays for SERT activity). Lumateperone is in Phase III clinical development as a treatment for schizophrenia, bipolar depression and agitation in dementia, including Alzheimer's Disease.

Lumateperone and related compounds have been disclosed in U.S. Pat. Nos. 6,548,493; 7,238,690; 6,552,017; 6,713,471; U.S. RE39680, and U.S. RE39679, as novel compounds useful for the treatment of disorders associated with 5-$HT_{2A}$ receptor modulation such as anxiety, depression, psychosis, schizophrenia, sleep disorders, sexual disorders, migraine, conditions associated with cephalic pain, and social phobias. PCT/US08/03340 and U.S. Pat. No. 7,081,455 also disclose methods of making substituted heterocycle fused gamma-carbolines and uses of these gamma-carbolines as serotonin agonists and antagonists useful for the control and prevention of central nervous system disorders such as addictive behavior and sleep disorders. WO 2009/145900 and U.S. Pat. No. 8,598,119, and WO 2013/155506 and US 2015/0080404, each incorporated herein by reference, disclose the use of specific substituted heterocycle fused gamma-carbolines for the treatment of a combination of psychosis and depressive disorders as well as sleep, depressive and/or mood disorders in patients with psychosis or Parkinson's disease and for the treatment or prophylaxis of disorders associated with dementia, particularly behavioral or mood disturbances such as agitation, irritation, aggressive/assaultive behavior, anger, physical or emotional outbursts and psychosis and sleep disorders associated with dementia. WO 2009/114181 and U.S. Pat. No. 8,648,077, each incorporated herein by reference, disclose methods of preparing toluenesulfonic acid addition salt crystals of particular substituted heterocycle fused gamma-carbolines, e.g., toluenesulfonic acid addition salt of 4-((6bR,10aS)-3-methyl-2,3,6b,9,10,10a-hexahydro-1H-pyrido[3',4': 4,5]pyrrolo[1,2,3-de]quinoxalin-8(7H)-yl)-1-(4-fluorophenyl)-1-butanone.

WO 2011/133224 and U.S. Pat. No. 8,993,572, each incorporated herein by reference, disclose prodrugs/metabolites of substituted heterocycle fused gamma-carboline for improved formulation, e.g., extended/controlled release formulation. This application discloses that heterocycle fused gamma-carboline N-substituted with a 4-fluorophenyl(4-hydroxy)butyl moiety are shown to have high selectivity for the serotonin transporter (SERT) relative to the heterocycle fused gamma-carboline containing 4-fluorophenylbutanone.

WO 2009/145900 (and U.S. Pat. No. 8,598,119) teaches that selected substituted heterocycle fused gamma-carboline compounds have nanomolar affinity for the serotonin reuptake transporter (SERT) and so are selective serotonin reuptake inhibitors.

As disclosed in WO2015/154025, US 2017/0183350, and WO 2017/165843, each incorporated herein by reference, deuterated forms of lumateperone and related compounds have been shown to have improved metabolic stability.

Conventional antidepressants often take weeks or months to achieve their full effects. For example, selective serotonin reuptake inhibitors (SSRIs), such as sertraline (Zoloft, Lustral), escitalopram (Lexapro, Cipralex), fluoxetine (Prozac), paroxetine (Seroxat), and citalopram, are considered first line therapies for depression, including major depressive disorder, due to their relatively mild side effects and broad effect on the symptoms of depression and anxiety. SSRIs, however, are generally not effective right away, and so are not particularly useful for acute treatment of depression. This delayed onset of action increases the risk for suicidal behavior. Benzodiazepines can be used for acute treatment of anxiety but can be addictive and have a high risk of overdose. Ketamine has recently been tested as a rapid-acting antidepressant for treatment-resistant depression, in bipolar disorder and major depressive disorder, but it has significant side effects and risk of overdose, and it is not orally active.

Over the last twenty years, at least six placebo-controlled clinical trials have studied ketamine as a rapid-acting antidepressant. In one study by Berman et al., involving 23 to 56-year old patients with major depressive episodes, it was found that a 40-minute infusion of ketamine at a total dose of 0.5 mg/kg resulted in significantly improved ratings on the Hamilton Depression Rating Scale (HDRS) compared to placebo after only 24 hours. Similar results were shown by Zarate et al. in 2006. Ketamine's effects begin as early 4 hours after intravenous infusion and can persist for up to 2 weeks. However, ketamine's approved medical uses are limited because of side effects, including perceptual disturbances, anxiety, dizziness, feelings of depersonalization and even psychosis (and it is a schedule III drug carrying risks of addiction and abuse). Ketamine also produces dissociative effects, such as hallucination and delirium, as well as analgesia and amnesia, none of which are associated with traditional antidepressants. These dissociative and other effects appear to be mediated by distinct cellular pathways from those which mediate the antidepressant effects of ketamine.

Unlike traditional antidepressants, which predominantly operate within the monoamine neurotransmitter sphere (i.e., serotonin, norepinephrine, and dopamine), ketamine is a selective NMDA receptor antagonist. The most widely prescribed current anti-depressants are SSRIs, monoamine oxidase inhibitors, and tricyclic antidepressants (primarily serotonin uptake, norepinephrine uptake, and/or dopamine uptake inhibitors). Ketamine acts through a separate system unrelated to the monoamines, and this is a major reason for its much more rapid effect. Ketamine directly antagonizes extrasynaptic glutamatergic NMDA receptors, which also indirectly results in activation of AMPA-type glutamate receptors. The downstream effects involve the brain-derived neurotrophic factor (BDNF) and mTOR (e.g., mTORC1) kinase pathways (signal transduction pathways).

Animal studies of depression have shown a link to reduction of mTOR (e.g., mTORC1) expression or activity. mTOR is a serine/threonine and tyrosine kinase which is a member of the phosphatidyl inositol 3-kinase family (PI3K family). It operates as a major component of the mTOR complex 1 (mTORC1) and the mTOR complex 2 (mTORC2). The mTOR pathways are central regulators of mammalian metabolism and physiology, with impacts on cell growth and survival, cytoskeleton organization, synaptic plasticity, memory retention, neuroendocrine regulation and neuronal recovery from stress (e.g. hypoxic stress). Studies have shown that activation of mTOR signaling reverses some of the synaptic and behavioral deficits caused by stressors, including chronic stress. There is evidence suggesting that ketamine's anti-depressant effects may be mediated through its activation of mTOR signaling (in combination with its promotion of the release of stored BDNF). Research has shown that a single antidepressant-effective dose of ketamine can induce a rapid-onset (within 30 minutes of administration) induction of phosphor-mTOR, as well as phospho-p70S6 kinase and phospho4EBP176, 177, in the prefrontal cortex and hippocampus of mice and rats. This suggests a mechanism whereby ketamine-induced protein translation occurs in an mTOR activation-dependent manner.

Ketamine (S-ketamine, or esketamine) was recently approved by the U.S. Food & Drug Administration (FDA) as a new treatment for treatment-resistant depression in adults (trade name Spravato). However, the approval came with several strict requirements and restrictions due to the observance of potentially severe side effects with ketamine treatment. For example, the FDA only approved Spravato for treatment in conjunction with an oral antidepressant, not as monotherapy, and requires that the drug be administered once or twice per week under the direct supervision of a healthcare provider. Moreover, patients are required to remain under observation for 2 hours after each dose, in order to watch for the most dangerous side effects-sedation, disassociation, and hypertension. Clinical studies also suggest a high risk of abuse and suicidal ideation.

Although 5-$HT_{2A}$ or 5-$HT_{2A}$/D2 receptor ligands are known to be useful for treating depression generally, they are not known for the acute treatment of depression or anxiety. New, fast-acting methods for the acute treatment of depression are urgently needed.

BRIEF SUMMARY OF THE INVENTION

We have surprisingly found that substituted heterocycle fused gamma-carbolines as described herein, particularly lumateperone, exhibit a fast-acting antidepressant action via indirect dopamine D1 receptor-dependent enhancement of NMDA and AMPA currents coupled with activation of the mTOR (e.g., mTORC1) signaling pathway, and paralleled by anti-inflammatory properties. Based on these data, the compounds described herein, such as lumateperone, are useful as orally-available, rapid-acting treatments for depression and anxiety, alone or in conjunction with other anti-anxiety or anti-depressant drugs, lacking the adverse side effects of ketamine and other current pharmacological approaches. In contrast to traditional treatments for depression, such as SSRIs, which typically have an onset of action 3-4 weeks after initiation of daily dosing, the unique pharmacological profile of the compounds described herein are predicted to result in immediate onset of action (e.g., hours to days after initial dosing). In addition, unlike benzodiazepine class agents, the compounds described herein appear to be non-addictive. They are therefore particularly suitable for the treatment of acute depressive episodes, including suicidal ideation and severe acute depression and/or severe acute anxiety.

The present disclosure thus provides a method for the acute treatment of depression and/or anxiety comprising administering an effective amount of (i) a 5-$HT_{2A}$ or 5-$HT_{2A}$/D2 receptor ligand, for example a substituted heterocycle fused gamma-carboline, as described herein, in free, pharmaceutically acceptable salt or prodrug form, to a patient in need thereof. The present disclosure further provides a method for enhancing mTOR signaling, e.g., in the brain, comprising administering an effective amount of (i) a 5-$HT_{2A}$ or 5-$HT_{2A}$/D2 receptor ligand, for example a substituted heterocycle fused gamma-carboline, as described herein, in free, pharmaceutically acceptable salt or prodrug form, to a patient in need thereof. The present disclosure further provides a method for reducing neuroinflammation, e.g., in the brain, comprising administering an effective amount of (i) 5-$HT_{2A}$ or 5-$HT_{2A}$/D2 receptor ligand, for example a substituted heterocycle fused gamma-carboline, as described herein, in free, pharmaceutically acceptable salt or prodrug form, to a patient in need thereof.

In some embodiments, the present disclosure provides the above methods, wherein such methods further comprise the concurrent administration of a PDE1 inhibitor, for example, the compounds of Formula II, as disclosed herein. Such compounds are disclosed in, for example, U.S. Pat. No. 9,545,406, the contents of which is hereby incorporated by reference in its entirety, as having utility in the treatment of central nervous system diseases, disorders and injuries, and as neuroprotective and/or neural regenerative agents. Such compounds are further disclosed in, for example, WO 2018/049417, the contents of which is hereby incorporated by reference in its entirety, as having utility in the treatment of diseases and disorders characterized by neuroinflammation.

BRIEF DESCRIPTION OF THE DRAWINGS

FIG. 3. Comparative serotonin transporter (SERT) inhibition among antipsychotic agents.

DETAILED DESCRIPTION

Figure 1:
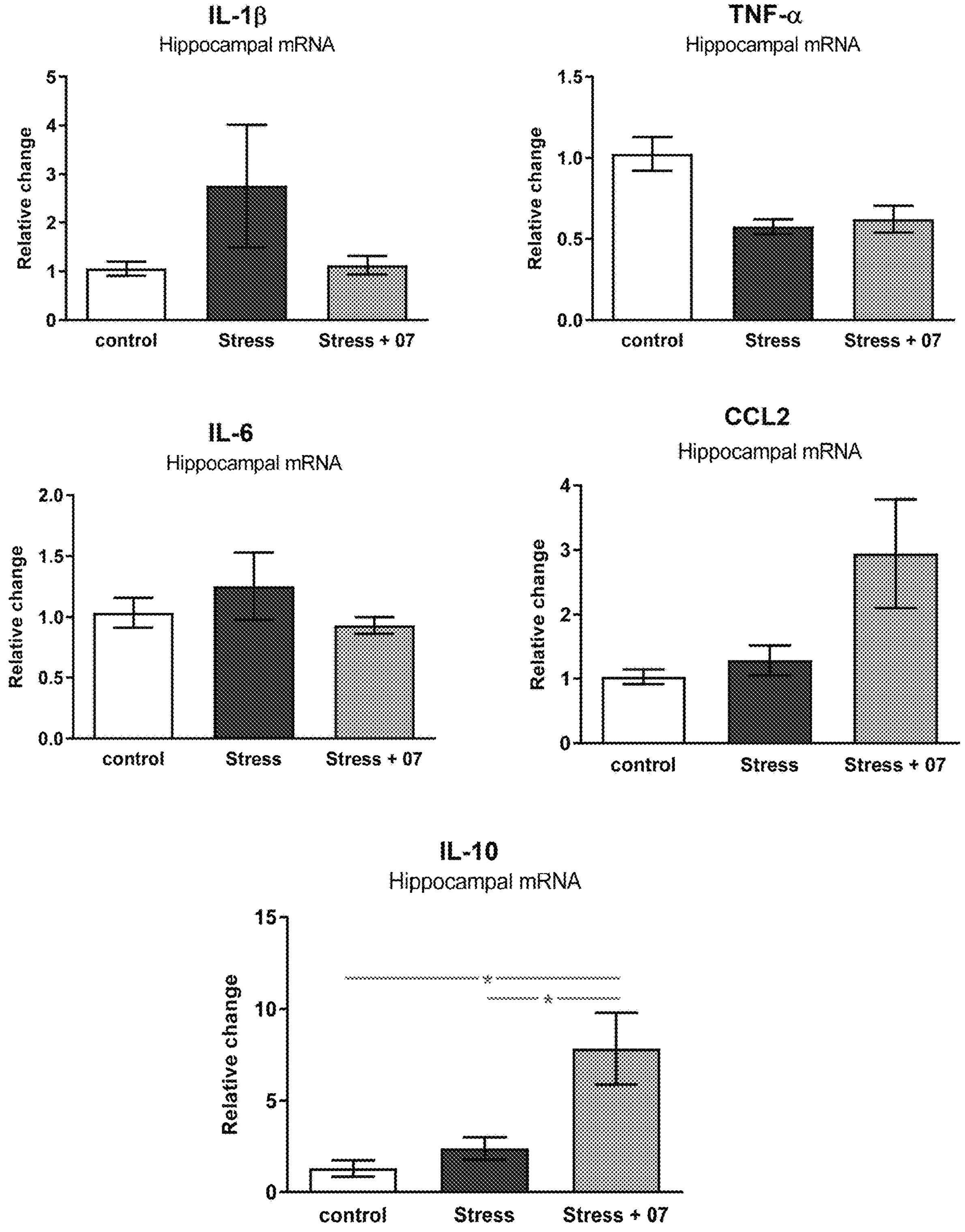
FIG. 1. Hippocampal pro- and anti-inflammatory cytokine expression measured by qPCR after mice were subjected to restraint stress.

Lumateperone is a novel therapeutic agent with potent (Ki=0.5 nM) binding to the 5-$HT_{2A}$ receptor and moderate binding to the D1 and D2 receptors and the SERT transporter. Functionally, such binding can generally result in either agonist activity, partial agonist activity, or antagonist activity. Lumateperone has been found to exhibit potent antagonist activity at the 5-$HT_{2A}$ receptor and SERT, and mixed agonist/antagonist activity at the D1 and D2 receptors (depending on cell type). In particular, lumateperone shows activity as a mesolimbic/mesocortical-selective dopamine receptor protein phosphorylation modulator consistent with presynaptic D2 receptor partial agonism and postsynaptic D2 receptor antagonism (Ki=32 nM) in vivo, with high D1 receptor affinity (Ki=52 nM), and inhibition of serotonin transporter activity (SERT) (Ki=26-62 nM, using different assays for SERT activity). Lumateperone is in Phase III clinical development as a treatment for schizophrenia, bipolar depression and agitation in dementia, including Alzheimer's Disease.

Low doses of an antipsychotic drug (APD) enhance the effectiveness of antidepressants in patients suffering from treatment-resistant depression (TRD) (Tohen et al., 2010). At the molecular level, combined application of low concentrations of antipsychotic drugs with selective serotonin uptake inhibitors (SSRIs) robustly and synergistically increase the activity of NMDA receptors on pyramidal neurons in the medial prefrontal cortex (mPFC). Further, combined application of an APD with an SSRI enhances AMPA receptor currents in the mPFC—an effect not seen with either treatment alone. Interestingly, this enhancement of glutamatergic neurotransmission in mPFC via both NMDA and AMPA receptors is mimicked by non-anesthetic doses of ketamine, an agent which provides rapid antidepressant efficacy in patients with TRD. Together, this data indicates that a combination of APD and SSRI properties is effective for alleviating TRD.

The inventors have found that lumateperone—possessing properties of an APD and an SSRI as a stand-alone agent—is found to enhance glutamatergic neurotransmission by effects on both NMDA and AMPA receptor conductance in rat mPFC slices. The actions of lumateperone are consistent with the effects of other rapid-acting antidepressant therapies, including the combined use of olanzapine (a D2-receptor antagonist APD) with fluoxetine (an SSRI) and of ketamine, thus supporting a molecular action of lumateperone consistent with an acute therapeutic action on anxiety and treatment-resistant depression.

In a particular embodiment, the present disclosure provides a method (Method 1) for the acute treatment of depression and/or anxiety comprising administering to a patient in need thereof, a therapeutically effective amount of a 5-$HT_{2A}$ or 5-$HT_{2A}$/D2 receptor ligand, for example, a compound of Formula I:

Formula I

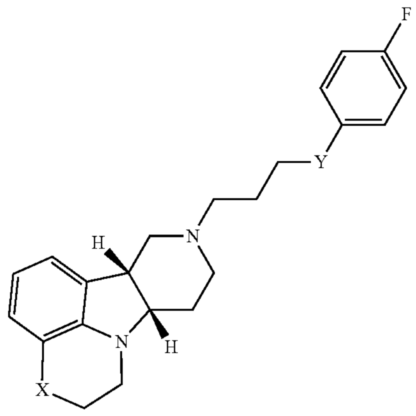

wherein:

X is —N(H)—, —N($CH_3$)— or —O—;

Y is —C(═O)—, —C(H)(OH)— or —C(H)($OR_1$)—;

$R_1$ is —C(O)—$C_{1-21}$alkyl (e.g., —C(O)—$C_{1-5}$alkyl, —C(O)—$C_{6-15}$alkyl or —C(O)—$C_{16-21}$alkyl), preferably said alkyl is a straight chain, optionally saturated or unsaturated and optionally substituted with one or more hydroxy or $C_{1-22}$alkoxy (e.g., ethoxy) groups, for example $R_1$ is —C(O)—$C_6$alkyl, —C(O)—$C_7$alkyl, C(O)—$C_9$alkyl, —C(O)—$C_{11}$alkyl, —C(O)—$C_{13}$alkyl or —C(O)—$C_{16}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand), optionally in deuterated form, in free, pharmaceutically acceptable salt or prodrug form.

For example, Method 1 may be as follows:

1.1. Method 1, wherein X in the compound of Formula I is —N(H)—, —N($CH_3$)— or —O—;

1.2. Method 1 or 1.1, wherein X in the compound of Formula I is —N(H);

1.3. Method 1 or 1.1, wherein X in the compound of Formula I is —N($CH_3$)—;

1.4. Method 1 or 1.1, wherein X in the compound of Formula I is —O—;

1.5. Method 1 or any of formulae 1.1-1.4, wherein Y in the compound of Formula I is —C(═O)—, —C(H)(OH)— or —C(H)($OR_1$)—;

1.6. Method 1 or any of formulae 1.1-1.4, wherein Y in the compound of Formula I is —C(═O)—;

1.7. Method 1 or any of formulae 1.1-1.4, wherein Y in the compound of Formula I is —C(H)(OH)—;

1.8. Method 1 or any of formulae 1.1-1.4, wherein Y in the compound of Formula I is —C(H)($OR_1$)—;

1.9. Method 1 or 1.8, wherein $R_1$ in the compound of Formula I is —C(O)—$C_{1-21}$alkyl (e.g., —C(O)—$C_{1-5}$alkyl, —C(O)—$C_{6-15}$alkyl or —C(O)—$C_{16-21}$alkyl), preferably said alkyl is a straight chain, optionally saturated or unsaturated and optionally substituted with one or more hydroxy or $C_{1-22}$alkoxy (e.g., ethoxy) groups, for example $R_1$ is —C(O)—$C_6$alkyl, —C(O)—$C_7$alkyl, —C(O)—$C_9$alkyl, —C(O)—$C_{11}$alkyl, —C(O)—$C_{13}$alkyl or —C(O)—$C_{15}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand); e.g., wherein $R_1$ in the compound of Formula I is —C(O)—$C_{6-15}$alkyl, e.g., —C(O)—$C_9$alkyl; or wherein $R_1$ in the compound of Formula I is —C(O)—$C_{1-5}$alkyl, e.g., —C(O)—$C_3$alkyl;

1.10. Method 1 or any of 1.1-1.5 or 1.7, wherein the Compound of Formula I is:

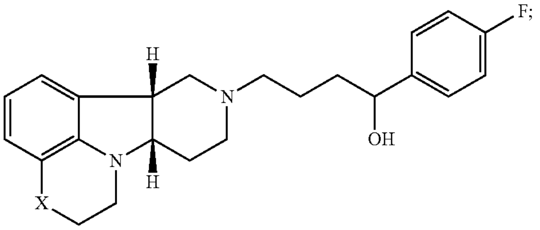

1.11. Method 1 or any of 1.1-1.5 or 1.7, wherein the Compound of Formula I is:

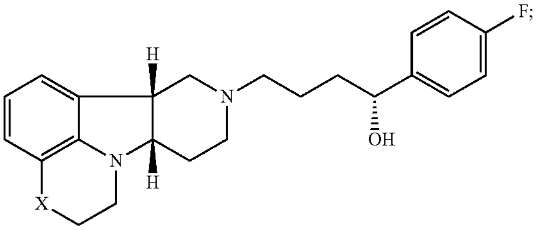

1.12. Any foregoing Method 1, or 1.1-1.3, 1.5, or 1.9 wherein the Compound of Formula I is:

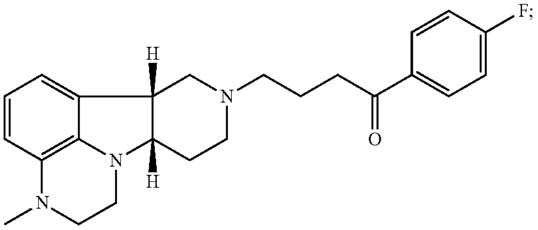 [SMILES: CN1CCN2c3c(cccc31)[C@@H]1CN(CCCC(=O)c3ccc(F)cc3)CC[C@@H]12]

1.13. Method 1.12 wherein the Compound of Formula I is in the form of the tosylate salt;

1.14. Method 1.12 wherein the Compound of Formula I is in the form of the free base;

1.15. Method 1 or any of 1.1-1.14 wherein the Compound of Formula I is in deuterated form, e.g., wherein the deuterium:protium ratio for a specified carbon-bound hydrogen atom is significantly higher, e.g., at least 2×, for example at least 10× higher, than the natural isotope ratios;

1.16. Method 1.15 wherein the Compound of Formula I is selected from

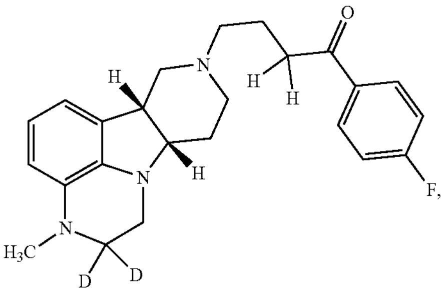

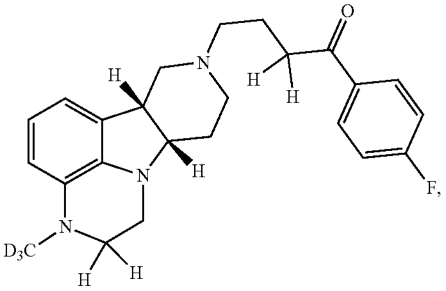

-continued

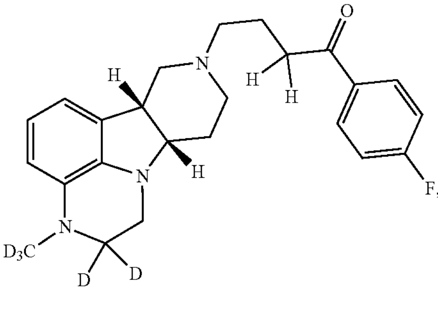

F, and

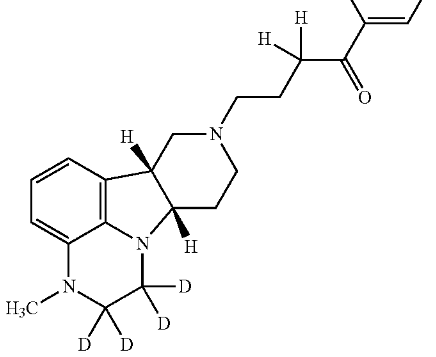

F;

wherein D represents a hydrogen position with substantially greater than natural deuterium incorporation (i.e., substantially greater than 0.0156%), e.g., greater than 60%, or greater than 70%, or greater than 80%, or greater than 90% or greater than 95%, or greater than 96%, or greater than 97%, or greater than 98%, or greater than 99%, in free or pharmaceutically acceptable salt form, e.g. tosylate salt form;

1.17. Any foregoing method, wherein the 5-$HT_{2A}$ or 5-$HT_{2A}$/D2 receptor ligand is a compound of Formula I in tosylate salt form, administered in a daily dose equivalent to 1 to 100 mg of free base, e.g., 1 to 75 mg, or 1 to 60 mg, or 1 to 40 mg, or 1 to 20 mg, or 1 to 10 mg, of free base;

1.18. Method 1.17 wherein the method comprises once daily administration of a unit dosage for oral administration, for example a tablet or capsule, comprising the compound of Formula I in tosylate salt form in an amount equivalent 1 to 100 mg of free base, e.g., 1 to 75 mg, or 1 to 60 mg, or 1 to 40 mg, or 1 to 20 mg, or 1 to 10 mg, of free base, and a pharmaceutically acceptable diluent or carrier;

1.19. Method 1.17 wherein the method comprises once daily administration of a unit dosage for subcutaneous or transmucosal administration, e.g., a sublingual or buccal orally disintegrating tablet or film, comprising the compound of Formula I in tosylate salt form in an amount equivalent to 0.5 to 30 mg of free base, e.g., 1-10 mg of free base, and a pharmaceutically acceptable diluent or carrier;

1.20. Any foregoing method wherein the condition to be treated is alleviated within one week, e.g., within three days, e.g., within one day;

1.21. Any foregoing method wherein the patient is diagnosed as having suicidal ideation and/or suicidal tendencies;

1.22. Any foregoing method wherein the condition to be treated is acute anxiety (e.g., a short-duration anxious episode associated with generalized anxiety disorder, panic disorder, specific phobias, or social anxiety disorder, or social avoidance);

1.23. Any foregoing method wherein the condition to be treated is acute depression (e.g., acute major depressive episode, acute short-duration depressive episode, acute recurrent brief depressive episode);

1.24. Any foregoing method wherein the condition to be treated is treatment resistant depression (e.g., depression which has not responded to treatment with an antidepressant agent selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof);

1.25. Any foregoing method wherein the condition to be treated is selected from bipolar depression and major depressive disorder;

1.26. Any foregoing method wherein the 5-$HT_{2A}$ or 5-$HT_{2A}$/D2 receptor ligand is in combination (e.g. a fixed combination in a unit dosage form, or a free combination administered sequentially or simultaneously or within a 24-hour period) with an effective amount of an additional anxiolytic or antidepressant agent;

1.27. Method 1.26 wherein the anxiolytic or antidepressant agent is selected from one or more compounds in free or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics, e.g. one or more compounds in free or pharmaceutically acceptable salt form, selected from:

(a) Selective serotonin reuptake inhibitors (SSRIs), e.g., Citalopram (Celexa), Escitalopram (Lexapro, Cipralex), Paroxetine (Paxil, Seroxat), Fluoxetine (Prozac), Fluvoxamine (Luvox) Sertraline (Zoloft, Lustral);

(b) Serotonin-norepinephrine reuptake inhibitors (SNRIs), e.g., Desvenlafaxine (Pristiq), Duloxetine (Cymbalta), Levomilnacipran (Fetzima), Milnacipran (Ixel, Savella), Tofenacin (Elamol, Tofacine), Venlafaxine (Effexor);

(c) Tricyclic antidepressants (TCAs), e.g., Amitriptyline (Elavil, Endep), Amitriptylinexide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Pipofezine (Azafen/Azaphen), Protriptyline (Vivactil), Trimipramine (Surmontil);

(d) Benzodiazepines, e.g., selected from 2-keto compounds (e.g., clorazepate, diazepam, flurazepam, halazepam, prazepam); 3-hydroxy compounds (lorazepam, lormetazepam, oxazepam, temazepam); 7-nitro compounds (e.g., clonazepam, flunitrazepam, nimetazepam, nitrazepam); triazolo compounds (e.g., adinazolam, alprazolam, estazolam, triazolam); and imidazo compounds (climazolam, loprazolam, midazolam);

1.28. Any foregoing method, wherein the method enhances mTOR (e.g., mTORC1) signaling (e.g., in the hippocampus, or in the brain, or in the pre-frontal cortex, or in the mPFC);

1.29. Any foregoing method wherein the method reduces neuroinflammation (e.g., by suppressing pro-inflammatory cytokine expression [IL-1β, IL-6, TNF-α, CCL2] and/or by enhancing anti-inflammatory cytokine expression [IL-4, IL-10]);

1.30. Method 1.29, wherein the neuroinflammation is caused by an infectious agent, e.g., a gram-negative bacterium (e.g., meningococcal meningitis);

1.31. Any foregoing method, wherein the compound of Formula I is administered intra-nasally, subcutaneously, intravenously, orally, or sub-lingually, or intra-peritoneally or bucally;

1.32. Any foregoing method, wherein the 5-$HT_{2A}$ or 5-$HT_{2A}$/D2 receptor ligand is administered to the patient concurrently with a PDE1 (cyclic nucleoside phosphodiesterase 1) inhibitor (e.g., administered simultaneously, separately or sequentially), in free or pharmaceutically acceptable salt form;

1.33. Method 1.32, wherein the PDE1 inhibitor is a compound according to Formula II:

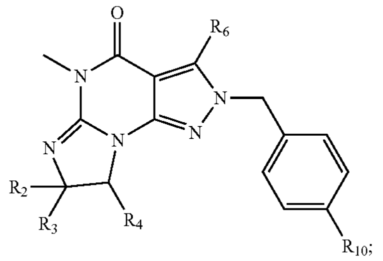

1.34. Method 1.33, wherein, in the Compound of Formula II, $R_6$ is phenylamino or 4-fluorophenylamino;

1.35. Method 1.33, wherein, in the Compound of Formula II, $R_{10}$ is 3-fluoropyrid-2-yl or methylcarbonyl;

1.36. Method 1.33, wherein, in the Compound of Formula II, $R_6$ is phenylamino or 4-fluorophenylamino and $R_{10}$ is 3-fluoropyrid-2-yl or methylcarbonyl;

1.37. Any Methods 1.33-1.36, wherein the Compound of Formula II is

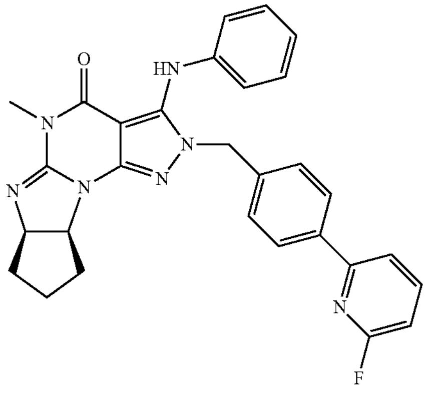

or

-continued

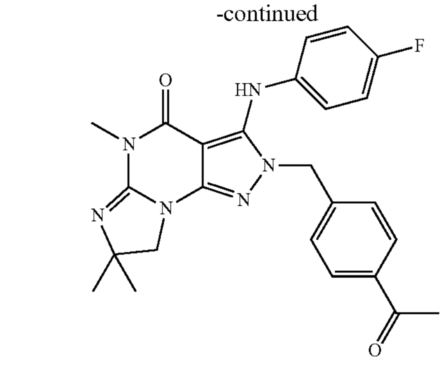

in free or pharmaceutically acceptable salt form.

1.38 Method 1.37, wherein the Compound of Formula II is in the form of the monophosphate salt;

1.39 Any of Methods 1.33-1.38, wherein the Compound of Formula I is:

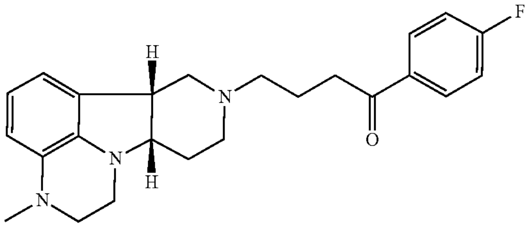 [SMILES: CN1CCN2c3c(cccc31)[C@@H]1CN(CCCC(=O)c3ccc(F)cc3)CC[C@@H]12]

in free or pharmaceutically acceptable salt form, e.g., tosylate salt form; and the Compound of Formula II is:

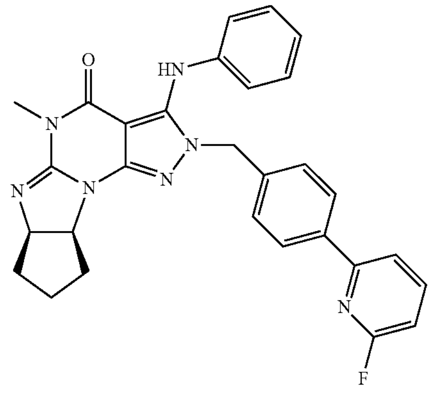 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form, e.g., monophosphate salt form;

1.40 Any of Methods 1.33-1.39, comprising administration of a pharmaceutical composition comprising effective amounts of both a Compound of Formula I and a Compound of Formula II;

1.41 Any foregoing method, wherein the method further comprises the concurrent administration of another anti-depressant agent (e.g., selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof), e.g., administered simultaneously, separately or sequentially;

1.42 Any foregoing method, wherein the method further comprises the concurrent administration of an NMDA receptor antagonist, for example, selected from ketamine (e.g., S-ketamine and/or R-ketamine), hydroxynorketamine, memantine, dextromethorphan, dextroallorphan, dextrorphan, amantadine, and agmatine, or any combination thereof, e.g., administered simultaneously, separately or sequentially;

1.43 Any foregoing method, wherein the method further comprises the concurrent administration of a NMDA receptor allosteric modulator, e.g., a NMDA receptor glycine-site modulator, such as rapastinel, nebostinel, apimostinel, D-cycloserine, or any combination thereof, e.g., administered simultaneously, separately or sequentially;

1.44 Any foregoing method, wherein the method provides the patient with an acute response to treatment with the therapeutic agent or agents (e.g., the Compound of Formula I, or the combination of the Compound or Formula I and the Compound of Formula II, and any additional antidepressant agents);

1.45 Method 1.44, wherein the patient shows an acute response to treatment within less than 3 weeks, for example, less than 2 weeks, or less than 1 week, or from 1 to 7 days, or 1 to 5 days, or 1 to 3 days, or 1 to 2 days, or about 1 day, or less than 2 days, or less than 1 day (e.g., 12-24 hours);

1.46 Any foregoing method, wherein the patient has not responded to, or has not responded adequately to, or who suffers undesirable side effects from, treatment with another antidepressant agent, for example, any one or more of a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor, or a serotonin receptor antagonist;

1.47 Any foregoing method, wherein the anxiety or depression is not associated with schizophrenia or dementia;

1.48 Any foregoing method, wherein the patient does not suffer from (or has not been diagnosed with) schizophrenia or dementia;

1.49 Any foregoing method, wherein the $5\text{-HT}_{2A}$ or $5\text{-HT}_{2A}$/D2 receptor ligand has an $IC_{50}$ of less than 250 nM or an $EC_{50}$ of less than 250 nM for activity (agonism and/or antagonism) at the $5\text{-HT}_{2A}$ receptor, e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

1.50 Any foregoing method, wherein the $5\text{-HT}_{2A}$ or $5\text{-HT}_{2A}$/D2 receptor ligand has an $IC_{50}$ of less than 250 nM or an $EC_{50}$ of less than 250 nM for activity (agonism and/or antagonism) at the D2 receptor, e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

1.51 Any foregoing method, wherein the $5\text{-HT}_{2A}$ or $5\text{-HT}_{2A}$/D2 receptor ligand has an $IC_{50}$ of less than 250 nM or an $EC_{50}$ of less than 250 nM for activity (agonism and/or antagonism) at the D1 receptor, e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

1.52 Any foregoing method, wherein the $5\text{-HT}_{2A}$ or $5\text{-HT}_{2A}$/D2 receptor ligand has an $IC_{50}$ of less than 250 nM or an $EC_{50}$ of less than 250 nM for activity (agonism and/or antagonism) at the serotonin transporter (SERT), e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said transporter (agonism or antagonism);

1.53 Any foregoing method, wherein the $5\text{-HT}_{2A}$ or $5\text{-HT}_{2A}$/D2 receptor ligand is a compound of Formula I in tosylate salt form, administered in the form of a long-acting injectable (LAI) composition, e.g., for intramuscular or subcutaneous injection;

1.54 Method 1.53, wherein the dose of the LAI composition is sufficient to provide the equivalent of a daily dose of 1 to 100 mg of free base, e.g., 1 to 75 mg, or 1 to 60 mg, or 1 to 40 mg, or 1 to 20 mg, or 1 to 10 mg, of free base, released over a period of time ranging from about 1 week to about 3 months, e.g., about 1 week to about 8 weeks, or about 1 week to about 6 weeks, or about 1 week to about 4 weeks, or about 1 week to about 3 weeks, or about 1 week to about 2 weeks;

1.55 Method 1.53 or 1.54, wherein the LAI composition comprises the compound of Formula I dissolved, dispersed, suspended, or encapsulated in a polymeric matrix;

1.56 Method 1.55, wherein the polymeric matrix comprises one or more biocompatible and biodegradable polymers as defined herein, e.g., poly(hydroxycarboxylic acids), poly(amino acids), cellulose polymers, modified cellulose polymers, polyamides, and polyesters;

1.57 Method 1.56, wherein the one or more polymers comprises polylactic acid, polyglycolic acid, polycitric acid, polymalic acid, poly-beta-hydroxybutyric acid, poly(lactic acid-glycolic acid) copolymer, 2-hydroxybutyric acid-glycolic acid copolymer, polylactic acid-polyethylene glycol copolymer, polyglycolic acid-polyethylene glycol copolymer, poly(alkyl alpha-cyanoacrylate) such as poly(butyl cyanoacrylate) or poly(2-octyl cyanoacrylate), poly(ortho ester), polycarbonate, polyortho-carbonate, a polyamino acid, (for example poly-gamma.-L-alanine, poly-. gamma.-benzyl-L-glutamic acid or poly-y-methyl-L-glutamic acid), and/or hyaluronic acid ester;

1.58 Method 1.56, wherein the one or more polymers comprises polylactic acid, polyglycolic acid, polycitric acid, polymalic acid, or a poly(lactic acid-glycolic acid) copolymer;

1.59 Method 1.56, wherein the one or more polymers comprises a poly(lactic acid-glycolic acid) copolymer, e.g., poly-d,l-lactide-co-glycolide;

1.60 Any foregoing method, wherein the $5\text{-HT}_{2A}$ or $5\text{-HT}_{2A}$/D2 receptor ligand is administered as monotherapy, e.g., it is not administered concurrently or in conjunction with an anti-depressant, anti-psychotic, or anti-anxiety agent;

1.61 Any foregoing method, wherein the $5\text{-HT}_{2A}$ or $5\text{-HT}_{2A}$/D2 receptor ligand is administered without the direct supervision of a health care professional (e.g., the compound is self-administered by the patient);

1.62 Any foregoing method, wherein the method does not comprise supervision or observation of the patient by a health care professional during or after (e.g., within 2 hours after) administration of a dose of the $5\text{-HT}_{2A}$ or $5\text{-HT}_{2A}$/D2 receptor ligand;

1.63 Any foregoing method, wherein the method does not put the patient at risk for sedation, dissociation, abuse, misuse, or suicidal ideation;

1.64 Any foregoing method, wherein the method does not result in hypertension (e.g., systolic and/or diastolic hypertension) within four hours after administration of a dose of the 5-$HT_{2A}$ or 5-$HT_{2A}$/D2 receptor ligand, e.g., an increase of more than 10 mm Hg, or more than 20 mm Hg, or more than 30 mm Hg, or more than 40 mm Hg, in systolic and/or diastolic blood pressure within 30 minutes to 4 hours after said dose;

1.65 Any foregoing method, wherein the method does not result in cognitive decline;

1.66 Any foregoing method, wherein the patient has (e.g., has been diagnosed with) or is at risk of aneurysmal vascular disease (e.g., thoracic aorta, abdominal aorta, intracranial, or peripheral arterial aneurysms), arteriovenous malformation or intracerebral hemorrhage;

1.67 Any foregoing method, wherein the patient is under concurrent treatment with an oral antidepressant selected from duloxetine, escitalopram, sertraline, or venlafaxine;

1.68 Any foregoing method, wherein the patient is not under concurrent treatment with an oral antidepressant selected from duloxetine, escitalopram, sertraline, or venlafaxine.

1.69 Any foregoing method, wherein the patient is unresponsive to, or cannot be treated with ketamine (e.g., S-ketamine), e.g., because it is contraindicated in said patient.

In another aspect, the disclosure provides a 5-$HT_{2A}$ or 5-$HT_{2A}$/D2 receptor ligand, e.g. a compound of Formula I, as hereinbefore described, for example lumateperone, in free or salt form, optionally in deuterated form, for use in the acute treatment of depression or anxiety, e.g., for use in any of Methods 1, et seq.

In another aspect, the disclosure provides the use of a 5-$HT_{2A}$ or 5-$HT_{2A}$/D2 receptor ligand, e.g. a compound of Formula I, as hereinbefore described, for example lumateperone, in free or salt form, optionally in deuterated form, in in the manufacture of a medicament for the acute treatment of depression or anxiety, e.g., for any of Methods 1, et seq.

In a particular embodiment, the present disclosure provides a method (Method 2) for the enhancing mTOR (e.g., mTORC1) signaling, e.g., in the brain (e.g., in the hippocampus, or in the prefrontal cortex, or in the mPFC) comprising administering to a patient in need thereof, a therapeutically effective amount of a 5-$HT_{2A}$ or 5-$HT_{2A}$/D2 receptor ligand, for example, a compound of Formula I:

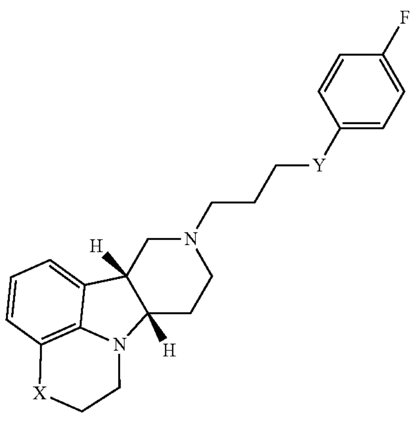

wherein:

X is —N(H)—, —N($CH_3$)— or —O—;

Y is —C(═O)—, —C(H)(OH)— or —C(H)($OR_1$)—;

$R_1$ is —C(O)—$C_{1-21}$alkyl (e.g., —C(O)—$C_{1-5}$alkyl, —C(O)—$C_{6-15}$alkyl or —C(O)—$C_{16-21}$alkyl), preferably said alkyl is a straight chain, optionally saturated or unsaturated and optionally substituted with one or more hydroxy or $C_{1-22}$alkoxy (e.g., ethoxy) groups, for example $R_1$ is —C(O)—$C_6$alkyl, —C(O)—$C_7$alkyl, —C(O)—$C_9$alkyl, —C(O)—$C_{11}$alkyl, —C(O)—$C_{13}$alkyl or —C(O)—$C_{15}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand), optionally in deuterated form, in free, pharmaceutically acceptable salt or prodrug form. For example, Method 2 may be as follows:

2.1. Method 2, wherein X in the compound of Formula I is —N(H)—, —N($CH_3$)— or —O—;

2.2. Method 2 or 2.1, wherein X in the compound of Formula I is —N(H);

2.3. Method 2 or 2.1, wherein X in the compound of Formula I is —N($CH_3$)—;

2.4. Method 2 or 2.1, wherein X in the compound of Formula I is —O—;

2.5. Method 2 or any of formulae 2.1-2.4, wherein Y in the compound of Formula I is —C(═O)—, —C(H)(OH)— or —C(H)($OR_1$)—;

2.6. Method 2 or any of formulae 1.1-1.4, wherein Y in the compound of Formula I is —C(═O)—;

2.7. Method 2 or any of formulae 2.11.1-2.4, wherein Y in the compound of Formula I is —C(H)(OH)—;

2.8. Method 2 or any of formulae 2.1-2.4, wherein Y in the compound of Formula I is —C(H)($OR_1$)—;

2.9. Method 2 or 2.8, wherein $R_1$ in the compound of Formula I is —C(O)—$C_{1-21}$alkyl (e.g., —C(O)—$C_{1-5}$alkyl, C(O)—$C_{6-15}$alkyl or —C(O)—$C_{16-21}$alkyl), preferably said alkyl is a straight chain, optionally saturated or unsaturated and optionally substituted with one or more hydroxy or $C_{1-22}$alkoxy (e.g., ethoxy) groups, for example $R_1$ is —C(O)—$C_6$alkyl, —C(O)—$C_7$alkyl, —C(O)—$C_9$alkyl, —C(O)—$C_{11}$alkyl, —C(O)—$C_{13}$alkyl or —C(O)—$C_{15}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand); e.g., wherein $R_1$ in the compound of Formula I is —C(O)—$C_{6-15}$alkyl, e.g., —C(O)—$C_9$alkyl; or wherein $R_1$ in the compound of Formula I is —C(O)—$C_{1-5}$alkyl, e.g., —C(O)—$C_3$alkyl;

2.10. Method 2 or any of 2.1-2.5 or 2.71.7, wherein the Compound of Formula I is:

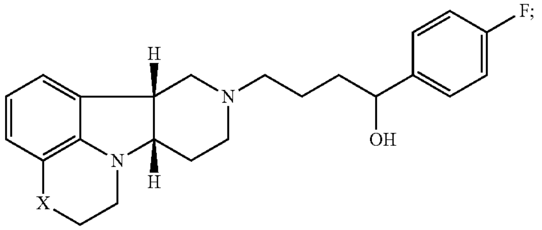

2.11. Method 2 or any of 1.1-1.5 or 7, wherein the Compound of Formula I is:

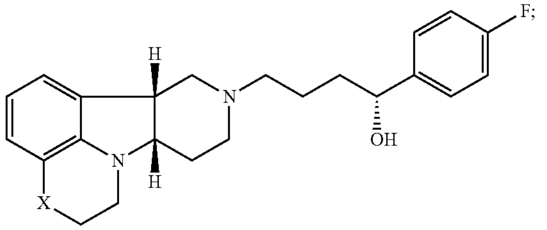

2.12. Any foregoing Method 2, or 2.1-2.3, 2.5, or 2.9 wherein the Compound of Formula I is:

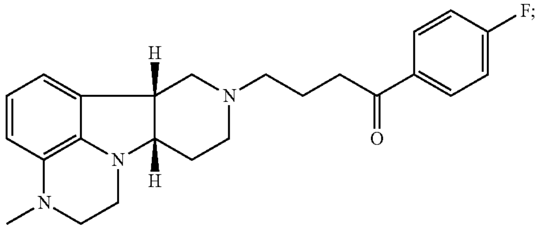 [SMILES: CN1CCN2c3c(cccc31)[C@@H]1CN(CCCC(=O)c3ccc(F)cc3)CC[C@@H]12]

2.13. Method 2.12, wherein the Compound of Formula I is in the form of the tosylate salt;

2.14. Method 2.12, wherein the Compound of Formula I is in the form of the free base;

2.15. Method 2 or any of 2.1-2.14, wherein the Compound of Formula I is in deuterated form, e.g., wherein the deuterium:protium ratio for a specified carbon-bound hydrogen atom is significantly higher, e.g., at least 2×, for example at least 10× higher, than the natural isotope ratios;

2.16. Method 2.15 wherein the Compound of Formula I is selected from

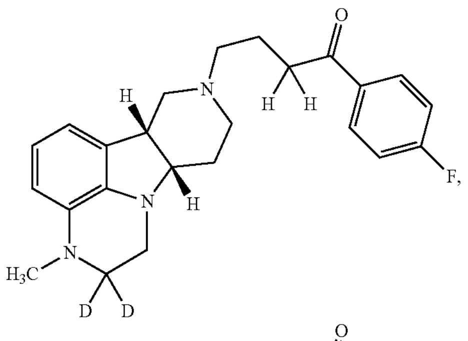

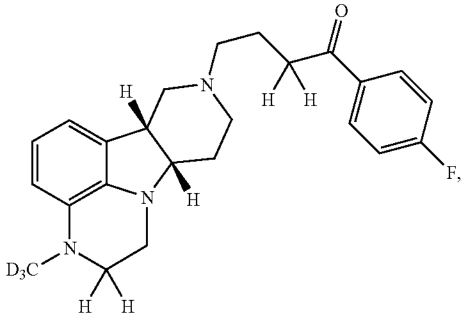

-continued

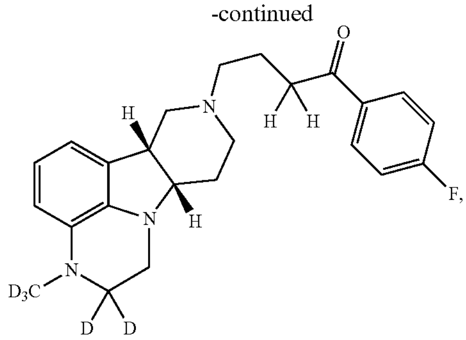

and

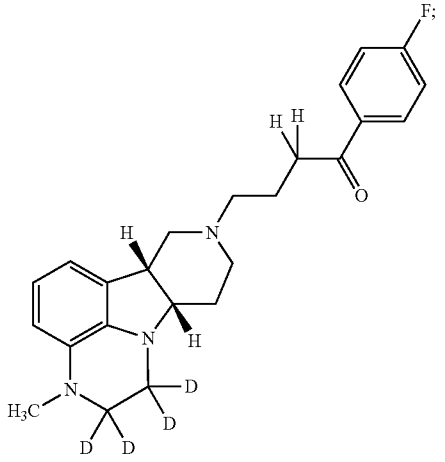

wherein D represents a hydrogen position with substantially greater than natural deuterium incorporation (i.e., substantially greater than 0.0156%), e.g., greater than 60%, or greater than 70%, or greater than 80%, or greater than 90% or greater than 95%, or greater than 96%, or greater than 97%, or greater than 98%, or greater than 99%, in free or pharmaceutically acceptable salt form, e.g. tosylate salt form;

2.17. Any foregoing method, wherein the 5-$HT_{2A}$ or 5-$HT_{2A}$/D2 receptor ligand is a compound of Formula I in tosylate salt form, administered in a daily dose equivalent to 1 to 100 mg of free base, e.g., 1 to 75 mg, or 1 to 60 mg, or 1 to 40 mg, or 1 to 20 mg, or 1 to 10 mg, of free base;

2.18. Method 2.17 wherein the method comprises once daily administration of a unit dosage for oral administration, for example a tablet or capsule, comprising the compound of Formula I in tosylate salt form in an amount equivalent to 1 to 100 mg of free base, e.g., 1 to 75 mg, or 1 to 60 mg, or 1 to 40 mg, or 1 to 20 mg, or 1 to 10 mg, of free base, and a pharmaceutically acceptable diluent or carrier;

2.19. Method 2.17 wherein the method comprises once daily administration of a unit dosage for subcutaneous or transmucosal administration, e.g., a sublingual or buccal orally disintegrating tablet or film, comprising the compound of Formula I in tosylate salt form in an amount equivalent to 0.5 to 30 mg of free base, e.g., 1-10 mg of free base, and a pharmaceutically acceptable diluent or carrier;

2.20. Any foregoing method wherein the mTOR (e.g., mTORC1) signaling is increased within one week, e.g., within three days, e.g., within one day;

2.21. Any foregoing method wherein the patient is diagnosed as having suicidal ideation and/or suicidal tendencies;

2.22. Any foregoing method wherein the patient is diagnosed with acute anxiety (e.g., a short-duration anxious episode associated with generalized anxiety disorder, panic disorder, specific phobias, or social anxiety disorder, or social avoidance);

2.23. Any foregoing method wherein the patient is diagnosed with acute depression (e.g., acute major depressive episode, acute short-duration depressive episode, acute recurrent brief depressive episode);

2.24. Any foregoing method wherein the patient is diagnosed with treatment resistant depression (e.g., depression which has not responded to treatment with an antidepressant agent selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof);

2.25. Any foregoing method wherein the patient is diagnosed with bipolar depression or major depressive disorder;

2.26. Any foregoing method wherein the 5-$HT_{2A}$ or 5-$HT_{2A}$/D2 receptor ligand in combination (e.g. a fixed combination in a unit dosage form, or a free combination administered sequentially or simultaneously or within a 24 hour period) with an effective amount of an addition anxiolytic or antidepressant agent;

2.27. Method 2.26 wherein the anxiolytic or antidepressant agent is selected from one or more compounds in free or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics, e.g. one or more compounds in free or pharmaceutically acceptable salt form, selected from:

(a) Selective serotonin reuptake inhibitors (SSRIs), e.g., Citalopram (Celexa), Escitalopram (Lexapro, Cipralex), Paroxetine (Paxil, Seroxat), Fluoxetine (Prozac), Fluvoxamine (Luvox) Sertraline (Zoloft, Lustral);

(b) Serotonin-norepinephrine reuptake inhibitors (SNRIs), e.g., Desvenlafaxine (Pristiq), Duloxetine (Cymbalta), Levomilnacipran (Fetzima), Milnacipran (Ixel, Savella), Tofenacin (Elamol, Tofacine), Venlafaxine (Effexor);

(c) Tricyclic antidepressants (TCAs), e.g., Amitriptyline (Elavil, Endep), Amitriptylinexide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Elronon, Nogedal), Pipofezine (Azafen/Azaphen), Protriptyline (Vivactil), Trimipramine (Surmontil);

(d) Benzodiazepines, e.g., selected from 2-keto compounds (e.g., clorazepate, diazepam, flurazepam, halazepam, prazepam); 3-hydroxy compounds (lorazepam, lormetazepam, oxazepam, temazepam); 7-nitro compounds (e.g., clonazepam, flunitrazepam, nimetazepam, nitrazepam); triazolo compounds (e.g., adinazolam, alprazolam, estazolam, triazolam); and imidazo compounds (climazolam, loprazolam, midazolam);

2.28. Any foregoing method wherein the method also reduces neuroinflammation (e.g., by suppressing pro-inflammatory cytokine expression [IL-1β, IL-6, TNF-α, CCL2] and/or by enhancing anti-inflammatory cytokine expression [IL-4, IL-10]);

2.29. Method 2.28, wherein the neuroinflammation is caused by an infectious agent, e.g., a gram-negative bacterium (e.g., meningococcal meningitis);

2.30. Any foregoing method, wherein the compound of Formula I is administered intra-nasally, subcutaneously, intravenously, orally, or sub-lingually, or intra-peritoneally or bucally;

2.31. Any foregoing method, wherein the 5-$HT_{2A}$ or 5-$HT_{2A}$/D2 receptor ligand is administered to the patient concurrently with a PDE1 (cyclic nucleoside phosphodiesterase 1) inhibitor (e.g., administered simultaneously, separately or sequentially), in free or pharmaceutically acceptable salt form;

2.32. Method 2.31, wherein the PDE1 inhibitor is a compound according to Formula II:

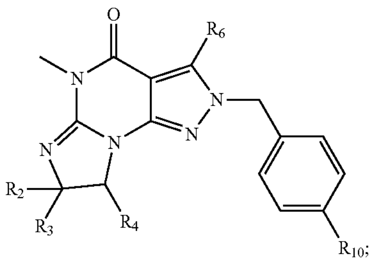

2.33. Method 2.32, wherein, in the Compound of Formula II, $R_6$ is phenylamino or 4-fluorophenylamino;

2.34. Method 2.32, wherein, in the Compound of Formula II, $R_{10}$ is 3-fluoropyrid-2-yl or methylcarbonyl;

2.35. Method 2.32, wherein, in the Compound of Formula II, $R_6$ is phenylamino or 4-fluorophenylamino and $R_{10}$ is 3-fluoropyrid-2-yl or methylcarbonyl;

2.36. Any Methods 2.32-2.35, wherein the Compound of Formula II is

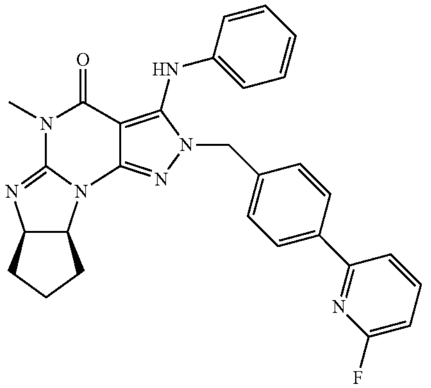

or

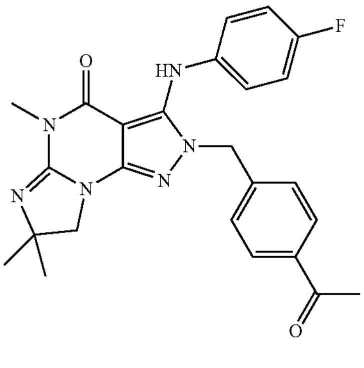

in free or pharmaceutically acceptable salt form.

2.37 Method 2.36, wherein the Compound of Formula II is in the form of the monophosphate salt;

2.38 Any of Methods 2.32-2.37, wherein the Compound of Formula I is:

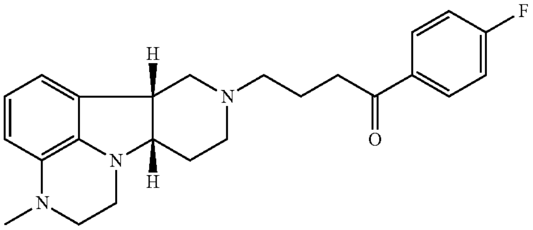 [SMILES: CN1CCN2c3c(cccc31)[C@@H]1CN(CCCC(=O)c3ccc(F)cc3)CC[C@@H]12]

in free or pharmaceutically acceptable salt form, e.g., tosylate salt form; and the Compound of Formula II is:

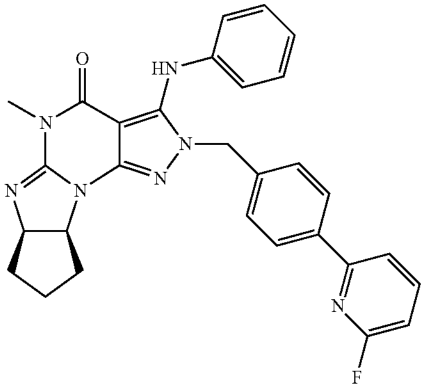 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form, e.g., monophosphate salt form;

2.39 Any of Methods 2.32-2.38, comprising administration of a pharmaceutical composition comprising effective amounts of both a Compound of Formula I and a Compound of Formula II;

2.40 Any foregoing method, wherein the method further comprises the concurrent administration of another antidepressant agent (e.g., selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor, a serotonin receptor antagonist, or any combination thereof), e.g., administered simultaneously, separately or sequentially;

2.41 Any foregoing method, wherein the method further comprises the concurrent administration of an NMDA receptor antagonist, for example, selected from ketamine (e.g., S-ketamine and/or R-ketamine), hydroxynorketamine, memantine, dextromethorphan, dextroallorphan, dextrorphan, amantadine, and agmatine, or any combination thereof, e.g., administered simultaneously, separately or sequentially;

2.42 Any foregoing method, wherein the method further comprises the concurrent administration of a NMDA receptor allosteric modulator, e.g., a NMDA receptor glycine-site modulator, such as rapastinel, nebostinel, apimostinel, D-cycloserine or any combination thereof, e.g., administered simultaneously, separately or sequentially;

2.43 Any foregoing method, wherein the method provides the patient with an acute response (e.g., an acute enhancement in mTOR (e.g., mTORC1) signaling) to treatment with the therapeutic agent or agents (e.g., the Compound of Formula I, or the combination of the Compound or Formula I and the Compound of Formula II, and any additional antidepressant agents);

2.44 Method 2.43, wherein the patient shows an acute response to treatment within less than 3 weeks, for example, less than 2 weeks, or less than 1 week, or from 1 to 7 days, or 1 to 5 days, or 1 to 3 days, or 1 to 2 days, or about 1 day, or less than 2 days, or less than 1 day (e.g., 12-24 hours);

2.45 Any foregoing method, wherein the 5-$HT_{2A}$ or 5-$HT_{2A}$/D2 receptor ligand has an $IC_{50}$ of less than 250 nM or an $EC_{50}$ of less than 250 nM for activity (agonism and/or antagonism) at the 5-$HT_{2A}$ receptor, e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

2.46 Any foregoing method, wherein the 5-$HT_{2A}$ or 5-$HT_{2A}$/D2 receptor ligand has an $IC_{50}$ of less than 250 nM or an $EC_{50}$ of less than 250 nM for activity (agonism and/or antagonism) at the D2 receptor, e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

2.47 Any foregoing method, wherein the 5-$HT_{2A}$ or 5-$HT_{2A}$/D2 receptor ligand has an $IC_{50}$ of less than 250 nM or an $EC_{50}$ of less than 250 nM for activity (agonism and/or antagonism) at the D1 receptor, e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

2.48 Any foregoing method, wherein the 5-$HT_{2A}$ or 5-$HT_{2A}$/D2 receptor ligand has an $IC_{50}$ of less than 250 nM or an $EC_{50}$ of less than 250 nM for activity (agonism and/or antagonism) at the serotonin transporter (SERT), e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said transporter (agonism or antagonism);

2.49 Any foregoing method, wherein the 5-$HT_{2A}$ or 5-$HT_{2A}$/D2 receptor ligand is a compound of Formula I in tosylate salt form, administered in the form of a long-acting injectable (LAI) composition, e.g., for intramuscular or subcutaneous injection;

2.50 Method 2.49, wherein the dose of the LAI composition is sufficient to provide the equivalent of a daily dose of 1 to 100 mg of free base, e.g., 1 to 75 mg, or 1 to 60 mg, or 1 to 40 mg, or 1 to 20 mg, or 1 to 10 mg, of free base, released over a period of time ranging from about 1 week to about 3 months, e.g., about 1 week to about 8 weeks, or about 1 week to about 6 weeks, or about 1 week to about 4 weeks, or about 1 week to about 3 weeks, or about 1 week to about 2 weeks;

2.51 Method 2.49 or 2.50, wherein the LAI composition comprises the compound of Formula I dissolved, dispersed, suspended, or encapsulated in a polymeric matrix;

2.52 Method 2.51, wherein the polymeric matrix comprises one or more biocompatible and biodegradable polymers as defined herein, e.g., poly(hydroxycarboxylic acids), poly(amino acids), cellulose polymers, modified cellulose polymers, polyamides, and polyesters;

2.53 Method 2.52, wherein the one or more polymers comprises polylactic acid, polyglycolic acid, polycitric acid, polymalic acid, poly-beta-hydroxybutyric acid, poly(lactic acid-glycolic acid) copolymer, 2-hydroxybutyric acid-glycolic acid copolymer, polylactic acid-polyethylene glycol copolymer, polyglycolic acid-polyethylene glycol copolymer, poly (alkyl alpha-cyanoacrylate) such as poly(butyl cyanoacrylate) or poly(2-octyl cyanoacrylate), poly(ortho ester), polycarbonate, polyortho-carbonate, a polyamino acid, (for example poly-gamma.-L-alanine, poly-. gamma.-benzyl-L-glutamic acid or poly-y-methyl-L-glutamic acid), and/or hyaluronic acid ester;

2.54 Method 2.52, wherein the one or more polymers comprises polylactic acid, polyglycolic acid, polycitric acid, polymalic acid, or a poly(lactic acid-glycolic acid) copolymer;

2.55 Method 2.52, wherein the one or more polymers comprises a poly(lactic acid-glycolic acid) copolymer, e.g., poly-d,l-lactide-co-glycolide;

2.56 Any foregoing method, wherein the 5-$HT_{2A}$ or 5-$HT_{2A}$/D2 receptor ligand is administered as monotherapy, e.g., it is not administered concurrently or in conjunction with an anti-depressant, anti-psychotic, or anti-anxiety agent;

2.57 Any foregoing method, wherein the 5-$HT_{2A}$ or 5-$HT_{2A}$/D2 receptor ligand is administered without the direct supervision of a health care professional (e.g., the compound is self-administered by the patient);

2.58 Any foregoing method, wherein the method does not comprise supervision or observation of the patient by a health care professional during or after (e.g., within 2 hours after) administration of a dose of the 5-$HT_{2A}$ or 5-$HT_{2A}$/D2 receptor ligand;

2.59 Any foregoing method, wherein the method does not put the patient at risk for sedation, dissociation, abuse, misuse, or suicidal ideation;

2.60 Any foregoing method, wherein the method does not result in hypertension (e.g., systolic and/or diastolic hypertension) within four hours after administration of a dose of the 5-$HT_{2A}$ or 5-$HT_{2A}$/D2 receptor ligand, e.g., an increase of more than 10 mm Hg, or more than 20 mm Hg, or more than 30 mm Hg, or more than 40 mm Hg, in systolic and/or diastolic blood pressure within 30 minutes to 4 hours after said dose;

2.61 Any foregoing method, wherein the method does not result in cognitive decline;

2.62 Any foregoing method, wherein the patient has (e.g., has been diagnosed with) or is at risk of aneurysmal vascular disease (e.g., thoracic aorta, abdominal aorta, intracranial, or peripheral arterial aneurysms), arteriovenous malformation or intracerebral hemorrhage;

2.63 Any foregoing method, wherein the patient is under concurrent treatment with an oral antidepressant selected from duloxetine, escitalopram, sertraline, or venlafaxine;

2.64 Any foregoing method, wherein the patient is not under concurrent treatment with an oral antidepressant selected from duloxetine, escitalopram, sertraline, or venlafaxine.

2.65 Any foregoing method, wherein the patient is unresponsive to, or cannot be treated with ketamine (e.g., S-ketamine), e.g., because it is contraindicated in said patient.

In another aspect, the disclosure provides a 5-$HT_{2A}$ or 5-$HT_{2A}$/D2 receptor ligand, e.g. a compound of Formula I, as hereinbefore described, for example lumateperone, in free or salt form, optionally in deuterated form, for use in the enhancement of mTOR (e.g., mTORC1) signaling, e.g., in the brain (e.g., in the hippocampus, or in the prefrontal cortex, or in the mPC), e.g., for use in any of Methods 2, et seq.

In another aspect, the disclosure provides the use of a 5-$HT_{2A}$ or 5-$HT_{2A}$/D2 receptor ligand, e.g. a compound of Formula I, as hereinbefore described, for example lumateperone, in free or salt form, optionally in deuterated form, in in the manufacture of a medicament for the enhancement of mTOR (e.g., mTORC1) signaling, e.g., in the brain (e.g., in the hippocampus, or in the prefrontal cortex, or in the mPC), e.g., for any of Methods 2, et seq.

In a particular embodiment, the present disclosure provides a method (Method 3) for reducing neuroinflammation, e.g., in the brain (e.g., in the prefrontal cortex, or in the mPC) comprising administering to a patient in need thereof, a therapeutically effective amount of a 5-$HT_{2A}$ or 5-$HT_{2A}$/D2 receptor ligand, for example, a compound of Formula I:

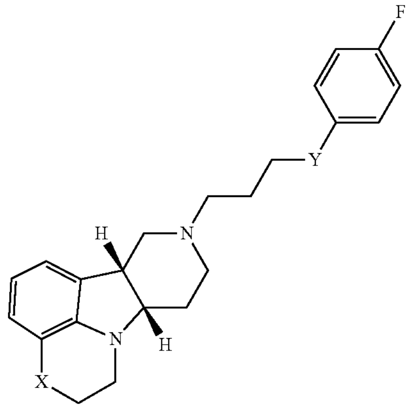

wherein:

X is —N(H)—, —N($CH_3$)— or —O—;

Y is —C(=O)—, —C(H)(OH)— or —C(H)($OR_1$)—;

$R_1$ is —C(O)—$C_{1-21}$alkyl (e.g., —C(O)—$C_{1-5}$alkyl, —C(O)—$C_{6-15}$alkyl or —C(O)—$C_{16-21}$alkyl), preferably said alkyl is a straight chain, optionally saturated or unsaturated and optionally substituted with one or more hydroxy or $C_{1-22}$alkoxy (e.g., ethoxy) groups, for example $R_1$ is —C(O)—$C_6$alkyl, —C(O)—$C_7$alkyl, —C(O)—$C_9$alkyl, —C(O)—$C_{11}$alkyl, —C(O)—$C_{13}$alkyl or —C(O)—$C_{15}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand), optionally in deuterated form, in free, pharmaceutically acceptable salt or prodrug form. For example, Method 3 may be as follows:

3.1. Method 3, wherein X in the compound of Formula I is —N(H)—, —N($CH_3$)— or —O—;

3.2. Method 3 or 3.1, wherein X in the compound of Formula I is —N(H);

3.3. Method 3 or 3.1, wherein X in the compound of Formula I is —N($CH_3$)—;

3.4. Method 3 or 3.1, wherein X in the compound of Formula I is —O—;

3.5. Method 3 or any of formulae 3.1-3.41.4, wherein Y in the compound of Formula I is —C(=O)—, —C(H)(OH)— or —C(H)($OR_1$)—;

3.6. Method 3 or any of formulae 3.1-3.4, wherein Y in the compound of Formula I is —C(═O)—;

3.7. Method 3 or any of formulae 3.1-3.4, wherein Y in the compound of Formula I is —C(H)(OH)—;

3.8. Method 3 or any of formulae 3.1-3.4, wherein Y in the compound of Formula I is —C(H)($OR_1$)—;

3.9. Method 3 or 3.8, wherein $R_1$ in the compound of Formula I is —C(O)—$C_{1-21}$alkyl (e.g., —C(O)—$C_{1-5}$alkyl, —C(O)—$C_{6-15}$alkyl or —C(O)—$C_{16-21}$alkyl), preferably said alkyl is a straight chain, optionally saturated or unsaturated and optionally substituted with one or more hydroxy or $C_{1-22}$alkoxy (e.g., ethoxy) groups, for example $R_1$ is —C(O)—$C_6$alkyl, —C(O)—$C_7$alkyl, —C(O)—$C_9$alkyl, —C(O)—$C_{11}$alkyl, —C(O)—$C_{13}$alkyl or —C(O)—$C_{15}$alkyl wherein such compound hydrolyzes to form the residue of a natural or unnatural, saturated or unsaturated fatty acid, e.g., the compound hydrolyzes to form the hydroxy compound on the one hand and octanoic acid, decanoic acid, dodecanoic acid, tetradecanoic acid or hexadecanoic acid on the other hand); e.g., wherein $R_1$ in the compound of Formula I is —C(O)—$C_{6-15}$alkyl, e.g., —C(O)—$C_9$alkyl; or wherein $R_1$ in the compound of Formula I is —C(O)—$C_{1-5}$alkyl, e.g., —C(O)—$C_3$alkyl;

3.10. Method 3 or any of 3.1-3.4 or 3.7, wherein the Compound of Formula I is:

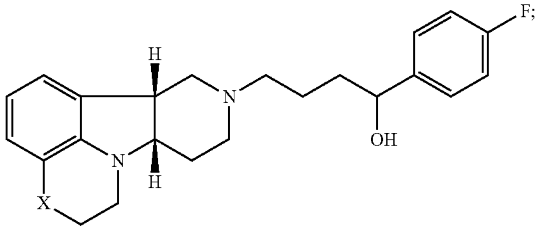

3.11. Method 3 or any of 3.1-3.4 or 3.7, wherein the Compound of Formula I is:

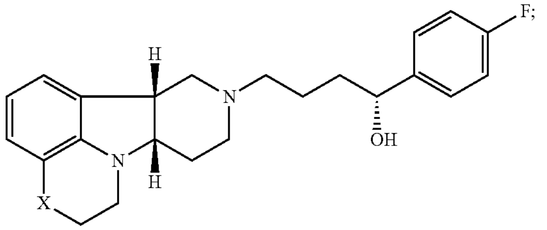

3.12. Any foregoing Method 3, or 3.1-3.3, 3.5, or 3.9 wherein the Compound of Formula I is:

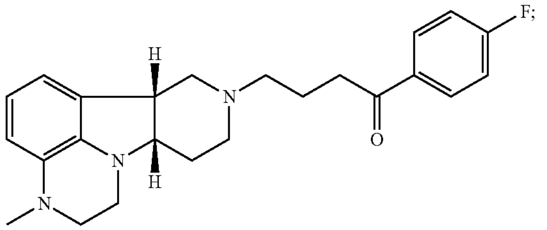 [SMILES: CN1CCN2c3c(cccc31)[C@@H]1CN(CCCC(=O)c3ccc(F)cc3)CC[C@@H]12]

3.13. Method 3.12, wherein the Compound of Formula I is in the form of the tosylate salt;

3.14. Method 3.12, wherein the Compound of Formula I is in the form of the free base;

3.15. Method 3 or any of 3.1-3.14, wherein the Compound of Formula I is in deuterated form, e.g., wherein the deuterium:protium ratio for a specified carbon-bound hydrogen atom is significantly higher, e.g., at least 2×, for example at least 10× higher, than the natural isotope ratios;

3.16. Method 3.15 wherein the Compound of Formula I is selected from

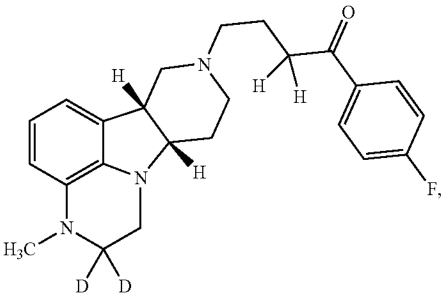

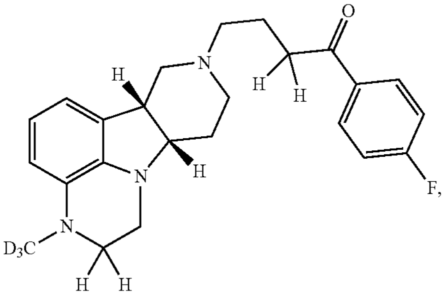

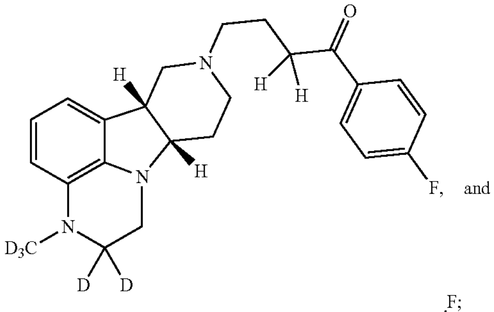

and

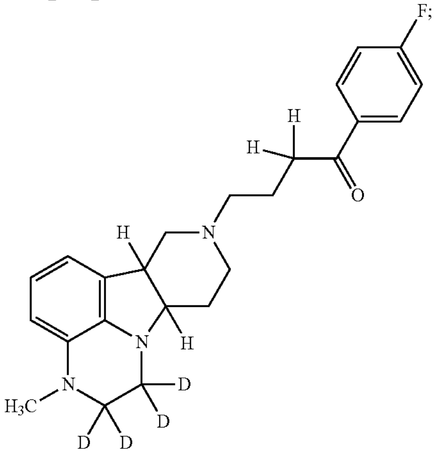

wherein D represents a hydrogen position with substantially greater than natural deuterium incorporation (i.e., substantially greater than 0.0156%), e.g., greater than 60%, or greater than 70%, or greater than 80%, or greater than 90% or greater than 95%, or greater than 96%, or greater than 97%, or greater than 98%, or greater than 99%, in free or pharmaceutically acceptable salt form, e.g. tosylate salt form;

3.17. Any foregoing method, wherein the 5-$HT_{2A}$ or 5-$HT_{2A}$/D2 receptor ligand is a compound of Formula I in tosylate salt form, administered in a daily dose equivalent to 1 to 100 mg of free base, e.g., 1 to 75 mg, or 1 to 60 mg, or 1 to 40 mg, or 1 to 20 mg, or 1 to 10 mg, of free base;

3.18. Method 3.17 wherein the method comprises once daily administration of a unit dosage for oral administration, for example a tablet or capsule, comprising the compound of Formula I in tosylate salt form in an amount equivalent to 1 to 100 mg of free base, e.g., 1 to 75 mg, or 1 to 60 mg, or 1 to 40 mg, or 1 to 20 mg, or 1 to 10 mg, of free base, and a pharmaceutically acceptable diluent or carrier;

3.19. Method 3.17 wherein the method comprises once daily administration of a unit dosage for subcutaneous or transmucosal administration, e.g., a sublingual or buccal orally disintegrating tablet or film, comprising the compound of Formula I in tosylate salt form in an amount equivalent to 0.5 to 30 mg of free base, e.g., 1-10 mg of free base, and a pharmaceutically acceptable diluent or carrier;

3.20. Any foregoing method wherein the neuroinflammation is reduced within one week, e.g., within three days, e.g., within one day;

3.21. Any foregoing method wherein the patient is diagnosed as having suicidal ideation and/or suicidal tendencies;

3.22. Any foregoing method wherein the patient is diagnosed with acute anxiety (e.g., a short-duration anxious episode associated with generalized anxiety disorder, panic disorder, specific phobias, or social anxiety disorder, or social avoidance);

3.23. Any foregoing method wherein the patient is diagnosed with acute depression (e.g., acute major depressive episode, acute short-duration depressive episode, acute recurrent brief depressive episode);

3.24. Any foregoing method wherein the patient is diagnosed with treatment resistant depression (e.g., depression which has not responded to treatment with an antidepressant agent selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof);

3.25. Any foregoing method wherein the patient is diagnosed with bipolar depression or major depressive disorder;

3.26. Any foregoing method wherein the 5-$HT_{2A}$ or 5-$HT_{2A}$/D2 receptor ligand in combination (e.g. a fixed combination in a unit dosage form, or a free combination administered sequentially or simultaneously or within a 24 hour period) with an effective amount of an addition anxiolytic or antidepressant agent;

3.27. Method 3.26 wherein the anxiolytic or antidepressant agent is selected from one or more compounds in free or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics, e.g. one or more compounds in free or pharmaceutically acceptable salt form, selected from:

(a) Selective serotonin reuptake inhibitors (SSRIs), e.g., Citalopram (Celexa), Escitalopram (Lexapro, Cipralex), Paroxetine (Paxil, Seroxat), Fluoxetine (Prozac), Fluvoxamine (Luvox) Sertraline (Zoloft, Lustral);

(b) Serotonin-norepinephrine reuptake inhibitors (SNRIs), e.g., Desvenlafaxine (Pristiq), Duloxetine (Cymbalta), Levomilnacipran (Fetzima), Milnacipran (Ixel, Savella), Tofenacin (Elamol, Tofacine), Venlafaxine (Effexor);

(c) Tricyclic antidepressants (TCAs), e.g., Amitriptyline (Elavil, Endep), Amitriptylinexide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Elronon, Nogedal), Pipofezine (Azafen/Azaphen), Protriptyline (Vivactil), Trimipramine (Surmontil);

(d) Benzodiazepines, e.g., selected from 2-keto compounds (e.g., clorazepate, diazepam, flurazepam, halazepam, prazepam); 3-hydroxy compounds (lorazepam, lormetazepam, oxazepam, temazepam); 7-nitro compounds (e.g., clonazepam, flunitrazepam, nimetazepam, nitrazepam); triazolo compounds (e.g., adinazolam, alprazolam, estazolam, triazolam); and imidazo compounds (climazolam, loprazolam, midazolam);

3.28. Any foregoing method, wherein the method also enhances mTOR (e.g., mTORC1) signaling (e.g., in brain tissue, or in the hippocampus, or in the pre-frontal cortex, or in the mPFC);

3.29. Any foregoing method wherein the method reduces neuroinflammation by suppressing pro-inflammatory cytokine expression [IL-1β, IL-6, TNF-α, CCL2], and/or by enhancing anti-inflammatory cytokine expression [IL-4, IL-10];

3.30. Any foregoing method, wherein the neuroinflammation is caused by or associated with any one or more of the following: an infectious agent, e.g., a gram-negative bacterium (e.g., meningococcal meningitis); a neurodegenerative condition, e.g., Alzheimer's disease, Parkinson's disease, amyotrophic lateral sclerosis, multiple sclerosis, or prion disease; intracerebral hemorrhage or intracerebral hypoxia; traumatic brain injury; and chemotherapy; conditions causing increased intracerebral levels of pro-inflammatory cytokines (e.g., IL-1β, IL-6, TNF-α, CCL2) and/or causing decreased levels of anti-inflammatory cytokines (e.g., IL-4 IL-10), or combinations thereof;

3.31. Any foregoing method, wherein the compound of Formula I is administered intra-nasally, subcutaneously, intravenously, orally, or sub-lingually, or intra-peritoneally or bucally;

3.32. Any foregoing method, wherein the 5-$HT_{2A}$ or 5-$HT_{2A}$/D2 receptor ligand is administered to the patient concurrently with a PDE1 (cyclic nucleoside phosphodiesterase 1) inhibitor (e.g., administered simultaneously, separately or sequentially), in free or pharmaceutically acceptable salt form;

3.33. Method 3.32, wherein the PDE1 inhibitor is a compound according to Formula II:

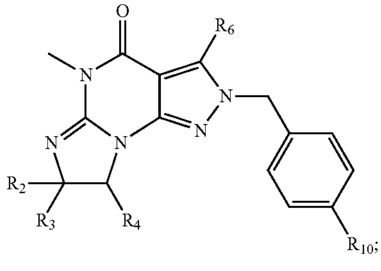

;

3.34. Method 3.33, wherein, in the Compound of Formula II, $R_6$ is phenylamino or 4-fluorophenylamino;

3.35. Method 3.33, wherein, in the Compound of Formula II, $R_{10}$ is 3-fluoropyrid-2-yl or methylcarbonyl;

3.36. Method 3.33, wherein, in the Compound of Formula II, $R_6$ is phenylamino or 4-fluorophenylamino and $R_{10}$ is 3-fluoropyrid-2-yl or methylcarbonyl;

3.37. Any Methods 3.33-3.36, wherein the Compound of Formula II is

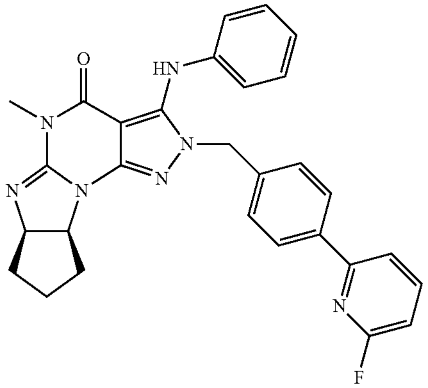

or

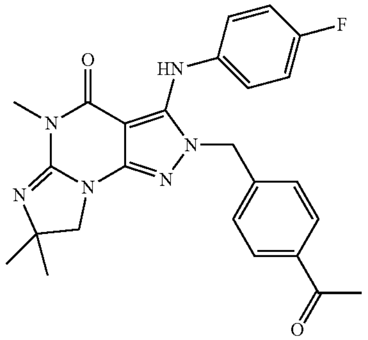

in free or pharmaceutically acceptable salt form.

3.38 Method 3.37, wherein the Compound of Formula II is in the form of the monophosphate salt;

3.39 Any of Methods 3.33-3.38, wherein the Compound of Formula I is:

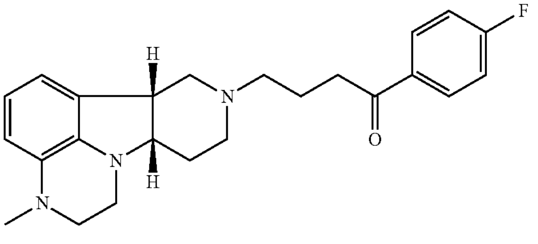 [SMILES: CN1CCN2c3c(cccc31)[C@@H]1CN(CCCC(=O)c3ccc(F)cc3)CC[C@@H]12]

in free or pharmaceutically acceptable salt form, e.g., tosylate salt form; and the Compound of Formula II is:

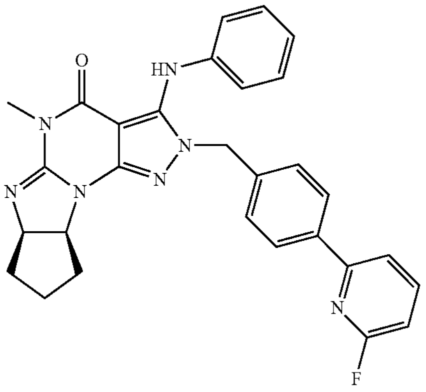 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form, e.g., monophosphate salt form;

3.40 Any of Methods 3.33-3.39, comprising administration of a pharmaceutical composition comprising effective amounts of both a Compound of Formula I and a Compound of Formula II;

3.41 Any foregoing method, wherein the method further comprises the concurrent administration of another antidepressant agent (e.g., selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor, a serotonin receptor antagonist, or any combination thereof), e.g., administered simultaneously, separately or sequentially;

3.42 Any foregoing method, wherein the method further comprises the concurrent administration of an NMDA receptor antagonist, for example, selected from ketamine (e.g., S-ketamine and/or R-ketamine), hydroxynorketamine, memantine, dextromethorphan, dextroallorphan, dextrorphan, amantadine, and agmatine, or any combination thereof, e.g., administered simultaneously, separately or sequentially;

3.43 Any foregoing method, wherein the method further comprises the concurrent administration of a NMDA receptor allosteric modulator, e.g., a NMDA receptor glycine-site modulator, such as rapastinel, nebostinel, apimostinel, D-cycloserine or any combination thereof, e.g., administered simultaneously, separately or sequentially;

3.44 Any foregoing method, wherein the method provides the patient with an acute response (e.g., an acute reduction in neuroinflammation) to treatment with the therapeutic agent or agents (e.g., the Compound of Formula I, or the combination of the Compound or Formula I and the Compound of Formula II, and any additional antidepressant agents);

3.45 Method 3.44, wherein the patient shows an acute response to treatment within less than 3 weeks, for example, less than 2 weeks, or less than 1 week, or from 1 to 7 days, or 1 to 5 days, or 1 to 3 days, or 1 to 2 days, or about 1 day, or less than 2 days, or less than 1 day (e.g., 12-24 hours)

3.46 Any foregoing method, wherein the 5-$HT_{2A}$ or 5-$HT_{2A}$/D2 receptor ligand has an $IC_{50}$ of less than 250 nM or an $EC_{50}$ of less than 250 nM for activity (agonism and/or antagonism) at the 5-$HT_{2A}$ receptor, e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

3.47 Any foregoing method, wherein the 5-$HT_{2A}$ or 5-$HT_{2A}$/D2 receptor ligand has an $IC_{50}$ of less than 250 nM or an $EC_{50}$ of less than 250 nM for activity (agonism and/or antagonism) at the D2 receptor, e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

3.48 Any foregoing method, wherein the 5-$HT_{2A}$ or 5-$HT_{2A}$/D2 receptor ligand has an $IC_{50}$ of less than 250 nM or an $EC_{50}$ of less than 250 nM for activity (agonism and/or antagonism) at the D1 receptor, e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism);

3.49 Any foregoing method, wherein the 5-$HT_{2A}$ or 5-$HT_{2A}$/D2 receptor ligand has an $IC_{50}$ of less than 250 nM or an $EC_{50}$ of less than 250 nM for activity (agonism and/or antagonism) at the serotonin transporter (SERT), e.g., an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said transporter (agonism or antagonism);

3.50 Any foregoing method, wherein the 5-$HT_{2A}$ or 5-$HT_{2A}$/D2 receptor ligand is a compound of Formula I in tosylate salt form, administered in the form of a long-acting injectable (LAI) composition, e.g., for intramuscular or subcutaneous injection;

3.51 Method 3.50, wherein the dose of the LAI composition is sufficient to provide the equivalent of a daily dose of 1 to 100 mg of free base, e.g., 1 to 75 mg, or 1 to 60 mg, or 1 to 40 mg, or 1 to 20 mg, or 1 to 10 mg, of free base, released over a period of time ranging from about 1 week to about 3 months, e.g., about 1 week to about 8 weeks, or about 1 week to about 6 weeks, or about 1 week to about 4 weeks, or about 1 week to about 3 weeks, or about 1 week to about 2 weeks;

3.52 Method 3.50 or 3.51, wherein the LAI composition comprises the compound of Formula I dissolved, dispersed, suspended, or encapsulated in a polymeric matrix;

3.53 Method 3.52, wherein the polymeric matrix comprises one or more biocompatible and biodegradable polymers as defined herein, e.g., poly(hydroxycarboxylic acids), poly(amino acids), cellulose polymers, modified cellulose polymers, polyamides, and polyesters;

3.54 Method 3.53, wherein the one or more polymers comprises polylactic acid, polyglycolic acid, polycitric acid, polymalic acid, poly-beta-hydroxybutyric acid, poly(lactic acid-glycolic acid) copolymer, 2-hydroxybutyric acid-glycolic acid copolymer, polylactic acid-polyethylene glycol copolymer, polyglycolic acid-polyethylene glycol copolymer, poly (alkyl alpha-cyanoacrylate) such as poly(butyl cyanoacrylate) or poly(2-octyl cyanoacrylate), poly(ortho ester), polycarbonate, polyortho-carbonate, a polyamino acid, (for example poly-gamma.-L-alanine, poly-. gamma.-benzyl-L-glutamic acid or poly-y-methyl-L-glutamic acid), and/or hyaluronic acid ester;

3.55 Method 3.53, wherein the one or more polymers comprises polylactic acid, polyglycolic acid, polycitric acid, polymalic acid, or a poly(lactic acid-glycolic acid) copolymer;

3.56 Method 3.53, wherein the one or more polymers comprises a poly(lactic acid-glycolic acid) copolymer, e.g., poly-d,l-lactide-co-glycolide;

3.57 Any foregoing method, wherein the 5-$HT_{2A}$ or 5-$HT_{2A}$/D2 receptor ligand is administered as monotherapy, e.g., it is not administered concurrently or in conjunction with an anti-depressant, anti-psychotic, or anti-anxiety agent;

3.58 Any foregoing method, wherein the 5-$HT_{2A}$ or 5-$HT_{2A}$/D2 receptor ligand is administered without the direct supervision of a health care professional (e.g., the compound is self-administered by the patient);

3.59 Any foregoing method, wherein the method does not comprise supervision or observation of the patient by a health care professional during or after (e.g., within 2 hours after) administration of a dose of the 5-$HT_{2A}$ or 5-$HT_{2A}$/D2 receptor ligand;

3.60 Any foregoing method, wherein the method does not put the patient at risk for sedation, dissociation, abuse, misuse, or suicidal ideation;

3.61 Any foregoing method, wherein the method does not result in hypertension (e.g., systolic and/or diastolic hypertension) within four hours after administration of a dose of the 5-$HT_{2A}$ or 5-$HT_{2A}$/D2 receptor ligand, e.g., an increase of more than 10 mm Hg, or more than 20 mm Hg, or more than 30 mm Hg, or more than 40 mm Hg, in systolic and/or diastolic blood pressure within 30 minutes to 4 hours after said dose;

3.62 Any foregoing method, wherein the method does not result in cognitive decline;

3.63 Any foregoing method, wherein the patient has (e.g., has been diagnosed with) or is at risk of aneurysmal vascular disease (e.g., thoracic aorta, abdominal aorta, intracranial, or peripheral arterial aneurysms), arteriovenous malformation or intracerebral hemorrhage;

3.64 Any foregoing method, wherein the patient is under concurrent treatment with an oral antidepressant selected from duloxetine, escitalopram, sertraline, or venlafaxine;

3.65 Any foregoing method, wherein the patient is not under concurrent treatment with an oral antidepressant selected from duloxetine, escitalopram, sertraline, or venlafaxine.

3.66 Any foregoing method, wherein the patient is unresponsive to, or cannot be treated with ketamine (e.g., S-ketamine), e.g., because it is contraindicated in said patient.

In another aspect, the disclosure provides a 5-$HT_{2A}$ or 5-$HT_{2A}$/D2 receptor ligand, e.g. a compound of Formula I, as hereinbefore described, for example lumateperone, in free or salt form, optionally in deuterated form, for use in the reduction of neuroinflammation, e.g., in the brain (e.g., in the hippocampus, or in the prefrontal cortex, or in the mPC), e.g., for use in any of Methods 3, et seq.

In another aspect, the disclosure provides the use of a 5-$HT_{2A}$ or 5-$HT_{2A}$/D2 receptor ligand, e.g. a compound of Formula I, as hereinbefore described, for example lumateperone, in free or salt form, optionally in deuterated form, in in the manufacture of a medicament for the reduction of neuroinflammation, e.g., in the brain (e.g., in the hippocampus, or in the prefrontal cortex, or in the mPC), e.g., for any of Methods 3, et seq.

The term "5-$HT_{2A}$ receptor ligand" refers to a compound which displays, at least, pharmacological activity at the serotonin 5-$HT_{2A}$ receptor, for example, compounds having an $IC_{50}$ of less than 250 nM or an $EC_{50}$ of less than 250 nM for activity (agonism and/or antagonism) at said receptor. In some embodiments, this term refers to a compound having an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at said receptor (agonism or antagonism).

The term "5-$HT_{2A}$/D2 receptor ligand" refers to a compound which displays, at least, pharmacological activity at both the serotonin 5-$HT_{2A}$ receptor and at the D2 receptor, for example, compounds having an $IC_{50}$ of less than 250 nM or an $EC_{50}$ of less than 250 nM for activity (agonism and/or antagonism) at each of said receptors. In some embodiments, this term refers to a compound having an $IC_{50}$ or $EC_{50}$ of less than 200 nM, or less than 150 nM, or less than 100 nM, or less than 75 nM, or less than 60 nM, or less than 50 nM, or less than 40 nM, or less than 30 nM, or less than 20 nM, for activity at one or both of these receptors (agonism or antagonism).

The words "treatment" and "treating" are to be understood accordingly as embracing prophylaxis and treatment or amelioration of symptoms of disease and/or treatment of the cause of the disease. In particular embodiments, the words "treatment" and "treating" refer to prophylaxis or amelioration of symptoms of the disease.

The term "patient" may include a human or non-human patient.

The Diagnostic and Statistical Manual of Mental Disorders, 5th Edition ("DSM-5"), defines "major depressive disorder" (MDD) as having five or more of a set of symptoms during the same two-week period of time, which symptoms represent a change from the patient's previous functioning. The five symptoms are selected from depressed mood, markedly diminished interest or pleasure in almost all activities, significant weight changes, insomnia or hyposomnia, psychomotor agitation or retardation, fatigue, feelings of worthlessness or excessive guilt, diminished ability to think or indecisiveness, and recurrent thoughts of death or suicidal ideation, wherein each of such symptoms is present nearly every day. At a minimum, MDD diagnosis requires at least depressed mood or loss of interest or pleasure as one of the five symptoms. MDD may consist of one or more "major depressive episodes" which can be spaced many weeks or months apart (more than 2 weeks apart to qualify as separate episodes). The DSM-5 notes that there is a risk of suicidal behavior at all time during a major depressive episode.

By its nature, MDD is an acute disorder in so far as the DSM-5 distinguishes it from "persistent depressive disorder", in which a patient has many of the same symptoms as for MDD, but which persists for at least a 2-year period. In addition to MDD, the DSM-5 also defines a "short-duration depressive episode" as having a depressed affect and at least four of the other symptoms which define MDD for at least 4 days, but less than 14 days. The DSM further defines "recurrent brief depression" as the concurrent presence of depressed mood and at least four other symptoms of depression for 2 to 13 days at least once per month, and persisting for at least 12 consecutive months. Thus, recurrent brief depression similarly consists of brief episodes of depression which recur regularly.

The DSM-5 also includes major depressive episodes as one of the diagnostic criteria for a patient suffering from bipolar disorder. Thus, a patient presenting a major depressive episode may be suffering from either major depressive disorder or bipolar disorder.

It is apparent that there are is a particular need for effective treatment of depression during the earliest stages of a major depressive episode, since each day of such episode can have profound consequences for a patient, yet typical SSRI anti-depressive agents take up to 2-4 weeks for beneficial effects to appear. The same is true for treatment of short duration depressive episodes as well as individual episodes of recurrent brief depression.

The DSM-5 categorizes what has traditionally been termed "post partum depression" or "peri-partum depression" as a merely a sub-type of the DSM's recognized depressive disorders, rather than as an independent depressive disorder. Thus, both major depressive disorder and acute depressive disorders can be diagnosed as being "with peripartum onset" (DSM-5 also does not distinguish peri- versus post-partum). Thus, as used herein, any of the depression indications may be considered to include such depression indication with peri-partum or post-partum onset, and thus, these indications embrace post-partum and peri-partum depression as well.

Thus, as used herein, the term "acute depression" refers to the initial period of what may be a brief or a chronic episode of depression (e.g., lasting 2 days to 2 weeks, or 2 weeks to 2 months, or 2 months to 2 years, or more). "Acute depression" may thus refer to the initial period of a major depressive episode, a short-duration depressive episode, or a recurrent brief depressive episode. There is a particular need in the art for the treatment of such acute stages of depressive episodes. A treatment initiated during this acute phase of depression may be continued indefinitely in those patients which respond thereto.

The DSM-5 defines a variety of anxiety disorders, including generalized anxiety disorder, panic disorder, social anxiety disorder, and specific phobias. Like the depressive disorders discussed above, anxiety disorders can be marked by recurrent episodes of short duration, such as panic attacks, which may persist over the course of a chronic disorder. For example, generalized anxiety disorder is defined by the DSM-5 to require excessive anxiety and worry occurring more days that not for at least 6 months, about a number of events or activities. A panic attack is defined as an abrupt surge of intense fear or intense discomfort that reaches a peak within minutes, but it can repeatedly recur in response to either expected stimuli or unexpected stimuli. Thus, as for the depressive disorders described above, there is a need for rapidly-acting anxiolytic agents that can treat the symptoms of anxiety or panic, yet some of the most common treatments for anxiety disorders are the SSRIs and other antidepressant agents which take 2-4 weeks to provide relief.

As used herein, "acute anxiety" refers to any short-duration episode of anxiety, e.g., lasting from one day or less to one week, which may be part of a chronic course of anxiety (e.g., lasting 2 days to 2 weeks, or 2 weeks to 2 months, or 2 months to 2 years, or more). "Acute anxiety" may thus include a panic attack or any specific instance of an anxious response to triggering stimuli or events (e.g., to the stimuli which trigger a specific phobia, the events which trigger social anxiety or generalized anxiety). There is a particular need in the art for the treatment of such acute stages of anxious episodes. A treatment initiated during this acute phase of anxiety may be continued indefinitely in those patients which respond thereto.

Social avoidance can be a critical and debilitating symptom in patients suffering from anxiety disorders, especially social anxiety disorder, as well as in patients suffering from traumatic anxiety disorders. Social avoidance is often one of the key determinants of whether a person with a severe anxiety disorder is capable of maintaining familial relationships or employment relationships. It has been unexpectedly found that certain substituted fused gamma carbolines having 5-$HT_{2A}$ and dopamine receptor activity, such as lumateperone, are effective in treating the emotional experience symptoms of psychiatric disorders (e.g., the emotional experience negative symptoms of schizophrenics). Negative symptoms of schizophrenia can be divided into two categories: emotional experience (e.g., emotional withdrawal, passive social withdrawal, active social avoidance) and emotional expression (e.g., blunted effect, poor rapport, lack of spontaneity, and motor retardation). In two clinical studies of patients with acute exacerbated schizophrenia, administration of lumateperone once daily (60 mg P.O.), for up to 28 days, resulted in a significant and unexpected improvement in symptoms of emotional experience compared to placebo. These are the symptoms that are most highly correlated with interpersonal functioning. As such, such compounds, including the compounds of Formula I, may be highly effective in treating the emotional experience symptoms of other psychiatric disorders, such as social anxiety disorders, or any other psychiatric disorders in which social withdrawal and social avoidance are symptoms.

If not otherwise specified or clear from context, the following terms herein have the following meanings:

"Alkyl" as used herein is a saturated or unsaturated hydrocarbon moiety, e.g., one to twenty-one carbon atoms in length, which may be linear or branched (e.g., n-butyl or tert-butyl), preferably linear, unless otherwise specified. For example, "$C_{1-21}$ alkyl" denotes alkyl having 1 to 21 carbon atoms. In one embodiment, alkyl is optionally substituted with one or more hydroxy or $C_{1-22}$alkoxy (e.g., ethoxy) groups. In another embodiment, alkyl contains 1 to 21 carbon atoms, preferably straight chain and optionally saturated or unsaturated, for example $R_1$ is an alkyl chain containing 1 to 21 carbon atoms, preferably 6-15 carbon atoms, 16-21 carbon atoms, e.g., so that together with the —C(O)— to which it attaches, e.g., when cleaved from the compound of Formula I, forms the residue of a natural or unnatural, saturated or unsaturated fatty acid.

The 5-$HT_{2A}$ or 5-$HT_{2A}$/D2 receptor ligand, for example a substituted heterocycle fused gamma-carbolines as described herein may be in free, pharmaceutically acceptable salt or prodrug form. Pharmaceutically acceptable salts include, for example, the tosylate salts in the case of Compounds of Formula I. Where dosages or amounts of a salt are given by weight, e.g., milligrams per day or milligrams per unit dose, the dosage amount of the salt is given as the weight of the corresponding free base, unless otherwise indicated.

In any and all embodiments described herein, the 5-$HT_{2A}$ or 5-$HT_{2A}$/D2 receptor ligand may also be a SERT ligand, i.e., said compounds may be a 5-$HT_{2A}$/SERT or a 5-$HT_{2A}$/D2/SERT receptor ligand.

In any and all embodiments described herein, the 5-$HT_{2A}$ or 5-$HT_{2A}$/D2 receptor ligand may be free or substantially free of any opioid receptor activity (e.g., free or substantially free of mu-opioid receptor activity, e.g., having an $IC_{50}$ greater than 50 nM or greater than 100 nM or greater than 150 nM).

The 5-$HT_{2A}$ or 5-$HT_{2A}$/D2 receptor ligand may in some cases also exist in prodrug form. A prodrug form is compound which converts in the body to the active compound. For example, compounds which contain hydroxy or carboxy substituents may form physiologically hydrolysable and acceptable esters. As used herein, "physiologically hydrolysable and acceptable ester" means esters which are hydrolysable under physiological conditions to yield acids (in the case of compounds which have hydroxy substituents) or alcohols (in the case of compounds which have carboxy substituents) which are themselves physiologically tolerable at doses to be administered. For example, wherein Y of the compound of Formula I is —C(H)($OR_1$), and $R_1$ is —C(O)—$C_{1-21}$alkyl, e.g., —C(O)—$C_3$alkyl or —C(O)—$C_9$alkyl, these compounds may hydrolyze under physiological condition to yield a compound of Formula I wherein Y is —C(H)(OH) on the one hand and $C_{1-21}$alkyl-C(O)OH, e.g., $C_3$alkyl-C(O) OH or $C_9$alkyl-C(O)OH on the other hand. As will be appreciated the term thus embraces conventional pharmaceutical prodrug forms. Wherein a prodrug (e.g., the compound of formula (I) wherein $R_1$ is —C(O)—$C_{1-21}$alkyl) is used, the dosage amount is calculated based on the amount of the compound of formula (I) wherein Y is —C(═O)— or —CH(OH)—, in free base form.

The term "concurrently" when referring to a therapeutic use means administration of two or more active ingredients to a patient as part of a regimen for the treatment of a disease or disorder, whether the two or more active agents are given at the same or different times or whether given by the same or different routes of administrations. Concurrent administration of the two or more active ingredients may be at different times on the same day, or on different dates or at different frequencies.

The term "simultaneously" when referring to a therapeutic use means administration of two or more active ingredients at or about the same time by the same route of administration.

The term "separately" when referring to a therapeutic use means administration of two or more active ingredients at or about the same time by different route of administration.

With respect to concurrent treatment using a 5-$HT_{2A}$ or 5-$HT_{2A}$/D2 receptor ligand (e.g., a compound of Formula I) and an NMDA receptor antagonist (e.g., ketamine), without being bound by theory, it is believed that the combination of these agents would permit lower doses of both agents to be used to treat depression, or other neuropsychiatric disorders described herein, such that the dissociative effects produced by the NMDA receptor antagonist would be minimized while the synergistic antidepressants effects would be maximized.

Dosages employed in practicing the present disclosure will of course vary depending, e.g. on the particular disease or condition to be treated, the particular active compounds used, the mode of administration, and the therapy desired. Unless otherwise indicated, an amount of an active compound for administration (whether administered as a free base or as a salt form) refers to or is based on the amount of the compound in free form (i.e., the calculation of the amount is based on the amount of active moiety in free form, not taking into account the weight of the counter ion in the case of a salt). Wherein a prodrug (e.g., the compound of formula (I) wherein $R_1$ is —C(O)—$C_{1-21}$alkyl) is used, the dosage amount is calculated based on the amount of the compound of formula (I) wherein Y is C(═O) in free base form. The 5-$HT_{2A}$ or 5-$HT_{2A}$/D2 receptor ligand may be administered by any suitable route, including orally, intramuscularly, subcutaneously, parenterally or transdermally, but are preferably administered orally. The 5-$HT_{2A}$ or 5-$HT_{2A}$/D2 receptor ligand may be administered by any suitable route, including oral, parenteral, transdermal, or transmucosal, for example in the form of a tablet, a capsule, a subcutaneous injection, or an oral, rapidly disintegrating tablet or film for sublingual or buccal administration.

For the avoidance of doubt, any disclosure of a numerical range, e.g., "up to X" amount is intended to include the upper numerical limit X. Therefore, a disclosure of "up to 60 mg" is intended to include 60 mg.

Pharmaceutical compositions comprising compounds of the Disclosure may be prepared using conventional diluents or excipients and techniques known in the galenic art. Thus, oral dosage forms may include tablets, capsules, solutions, suspensions and the like.

Compounds of the present disclosure may be included as a depot formulation, e.g., by dispersing, dissolving, suspending, or encapsulating the Compounds of the Invention in a polymeric matrix as described in herein, such that the Compound is continually released as the polymer degrades over time. The release of the Compounds of the Invention from the polymeric matrix provides for the controlled-and/or delayed- and/or sustained-release of the Compounds, e.g., from the pharmaceutical depot composition, into a subject, for example a warm-blooded animal such as man, to which the pharmaceutical depot is administered. Thus, the pharmaceutical depot delivers the Compounds of the Invention to the subject at concentrations effective for treatment of the particular disease or medical condition over a sustained period of time, e.g., 1 week to 3 months.

Polymers useful for the polymeric matrix in the Composition of the Invention (e.g., Depot composition of the Invention) may include a polyester of a hydroxyfatty acid and derivatives thereof or other agents such as polylactic acid, polyglycolic acid, polycitric acid, polymalic acid, poly-beta.-hydroxybutyric acid, epsilon.-capro-lactone ring opening polymer, lactic acid-glycolic acid copolymer, 2-hydroxybutyric acid-glycolic acid copolymer, polylactic acid-polyethyleneglycol copolymer or polyglycolic acid-polyethyleneglycol copolymer), a polymer of an alkyl alpha-cyanoacrylate (for example poly(butyl 2-cyanoacrylate)), a polyalkylene oxalate (for example polytrimethylene oxalate or polytetramethylene oxalate), a polyortho ester, a polycarbonate (for example polyethylene carbonate or polyethylenepropylene carbonate), a polyortho-carbonate, a polyamino acid (for example poly-gamma.-L-alanine, poly-.gamma.-benzyl-L-glutamic acid or poly-y-methyl-L-glutamic acid), a hyaluronic acid ester, and the like, and one or more of these polymers can be used.

If the polymers are copolymers, they may be any of random, block and/or graft copolymers. When the above alpha-hydroxycarboxylic acids, hydroxydicarboxylic acids and hydroxytricarboxylic acids have optical activity in their molecules, any one of D-isomers, L-isomers and/or DL-isomers may be used. Among others, alpha-hydroxycarboxylic acid polymer (preferably lactic acid-glycolic acid polymer), its ester, poly-alpha-cyanoacrylic acid esters, etc. may be used, and lactic acid-glycolic acid copolymer (also referred to as poly(lactide-alpha-glycolide) or poly(lactic-co-glycolic acid), and hereinafter referred to as PLGA) are preferred. Thus, in one aspect the polymer useful for the polymeric matrix is PLGA. As used herein, the term PLGA includes polymers of lactic acid (also referred to as polylactide, poly(lactic acid), or PLA). Most preferably, the polymer is the biodegradable poly(d,l-lactide-co-glycolide) polymer, such as PLGA 50:50, PLGA 85:15 and PLGA 90:10.

In a preferred embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body. Particular useful examples of polymeric matrix materials include poly (glycolic acid), poly-D,L-lactic acid, poly-L-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. The preferred polymer for use in the practice of this invention is dl(polylactide-co-glycolide). It is preferred that the molar ratio of lactide to glycolide in such a copolymer be in the range of from about 75:25 to 50:50.

Useful PLGA polymers may have a weight-average molecular weight of from about 5,000 to 500,000 Daltons, preferably about 150,000 Daltons. Dependent on the rate of degradation to be achieved, different molecular weight of polymers may be used. For a diffusional mechanism of drug release, the polymer should remain intact until all of the drug is released from the polymeric matrix and then degrade. The drug can also be released from the polymeric matrix as the polymeric excipient bioerodes.

The PLGA may be prepared by any conventional method, or may be commercially available. For example, PLGA can be produced by ring-opening polymerization with a suitable catalyst from cyclic lactide, glycolide, etc. (see EP-0058481B2; Effects of polymerization variables on PLGA properties: molecular weight, composition and chain structure).

It is believed that PLGA is biodegradable by means of the degradation of the entire solid polymer composition, due to the break-down of hydrolysable and enzymatically cleavable ester linkages under biological conditions (for example in the presence of water and biological enzymes found in tissues of warm-blooded animals such as humans) to form lactic acid and glycolic acid. Both lactic acid and glycolic acid are water-soluble, non-toxic products of normal metabolism, which may further biodegrade to form carbon dioxide and water. In other words, PLGA is believed to degrade by means of hydrolysis of its ester groups in the presence of water, for example in the body of a warm-blooded animal such as man, to produce lactic acid and glycolic acid and create the acidic microclimate. Lactic and glycolic acid are by-products of various metabolic pathways in the body of a warm-blooded animal such as man under normal physiological conditions and therefore are well tolerated and produce minimal systemic toxicity.

Example 1: Lumateperone is a Rapid-Acting Antidepressant: Effects on mTOR Signaling, Stress and Inflammation Summary The Compound of Formula I, wherein X is $N(CH_3)$, Y is C=O, i.e., lumateperone (ITI-007):

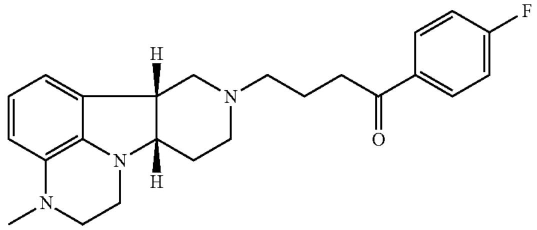 [SMILES: CN1CCN2c3c(cccc31)[C@@H]1CN(CCCC(=O)c3ccc(F)cc3)CC[C@@H]12]

in the form of its tosylate salt, is an investigational new drug in Phase III clinical development as a treatment for schizophrenia, bipolar depression and agitation associated with dementia, including Alzheimer's Disease. Lumateperone provides selective and simultaneous modulation of serotonin, dopamine and glutamate neurotransmission and is particularly of interest in the context of psychiatric disorders.

We have discovered that lumateperone enhances both NMDA and AMPA-induced currents in rat mPFC pyramidal neurons via activation of D1 receptors, which suggests that lumateperone acts similarly to fast-acting antidepressants, such as ketamine. We have also elucidated the intracellular signaling and gene expression pathways altered by lumateperone in different rodent models.

Given that psychiatric disorders such as schizophrenia, major depressive disorder and other neurological conditions are accompanied by increased neuroinflammation, in a second study, we investigate the potential anti-inflammatory properties of lumateperone. Using qPCR, NanoString and Multiplex immunoassay, samples are analyzed from mice subjected to an acute immune challenge (LPS, 500 μg/kg). Lumateperone is found to suppress pro-inflammatory cytokines in the brain, while enhancing expression of anti-inflammatory cytokines in response to an inflammogen treatment. In a follow-up study, we submit mice to a more naturalistic cause of inflammation, using acute restraint stress, and confirm that lumateperone is able to inhibit the stress-induced increased expression of pro-inflammatory cytokines, both in brain and serum.

LPS-Induced Stress Experiments

Figure 9:
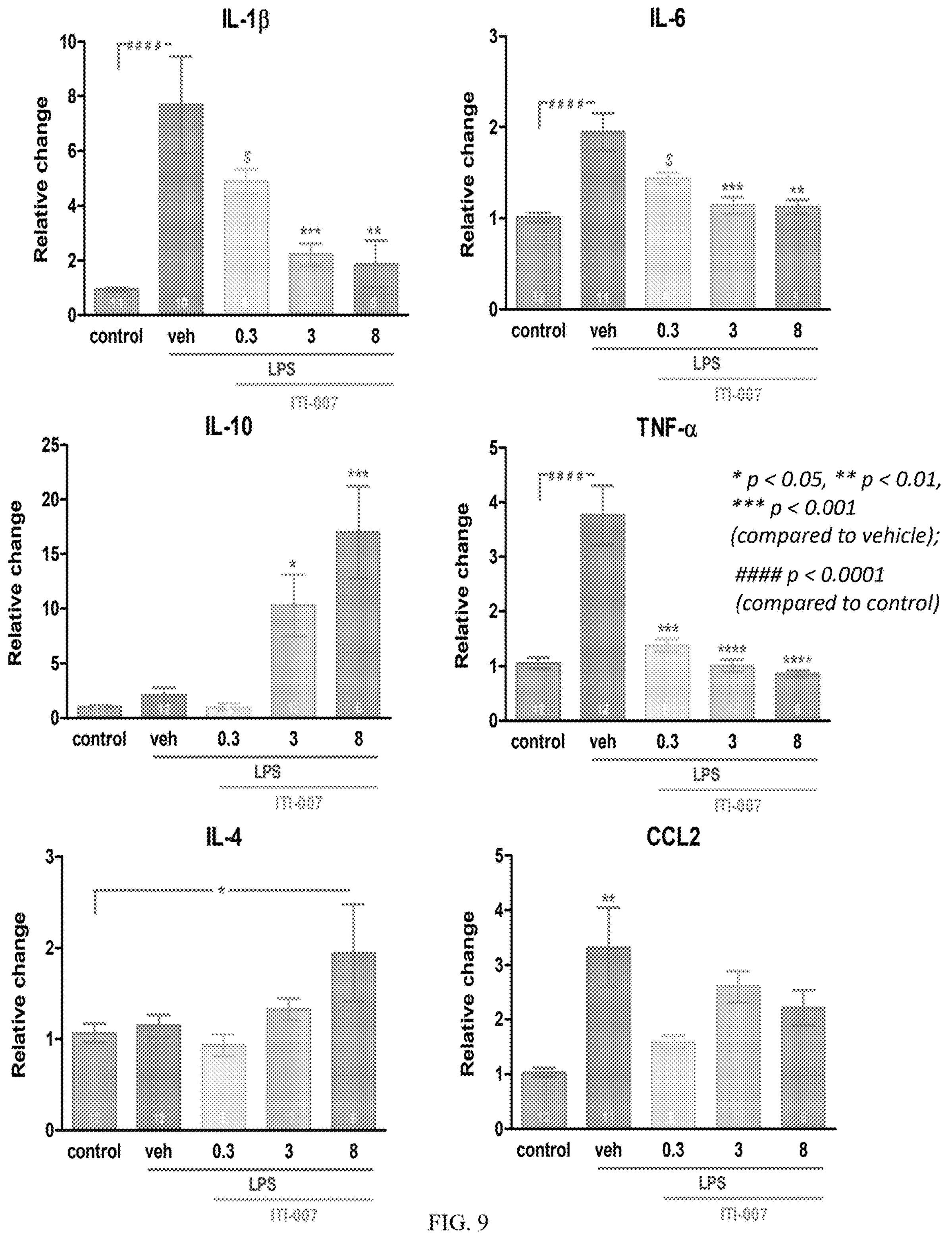
FIG. 9. Hippocampal pro- and anti-inflammatory cytokine expression measured by qPCR after mice were concurrently injected with lipopolysaccharide (LPS) and test compound.

Male, C57/B16 mice (n=6-12/group) are divided into five groups-control (vehicle/saline), vehicle/LPS, and ITI-007/LPS at three different doses of ITI-007. Mice are first injected i.p. with either vehicle (5% DMSO, 5% Tween, 15% PEG, 75% water) or ITI-007 at 0.3 mg/kg, 3.0 mg/kg or 8.0 mg/kg. The mice are then immediately injected s.c. with either 0.9% saline or with 500 μg/kg lipopolysaccharide (LPS) diluted in 0.9% saline. After two hours, the animals are sacrificed, and hippocampal slices are obtained and analyzed for cytokine mRNA using qPCR. The results are shown in FIG. 9, normalized to the control group using the delta ct method. The results demonstrate that co-injection of lumateperone with LPS alters hippocampal cytokine response, with significantly attenuated production of pro-inflammatory cytokine mRNA (IL-1β, IL-6, TNFα, CCL2), and significantly enhanced production of anti-inflammatory cytokine mRNA (IL-4, IL-10). The results also substantially show a dose-response effect with increasing dose of lumateperone.

Figure 10:
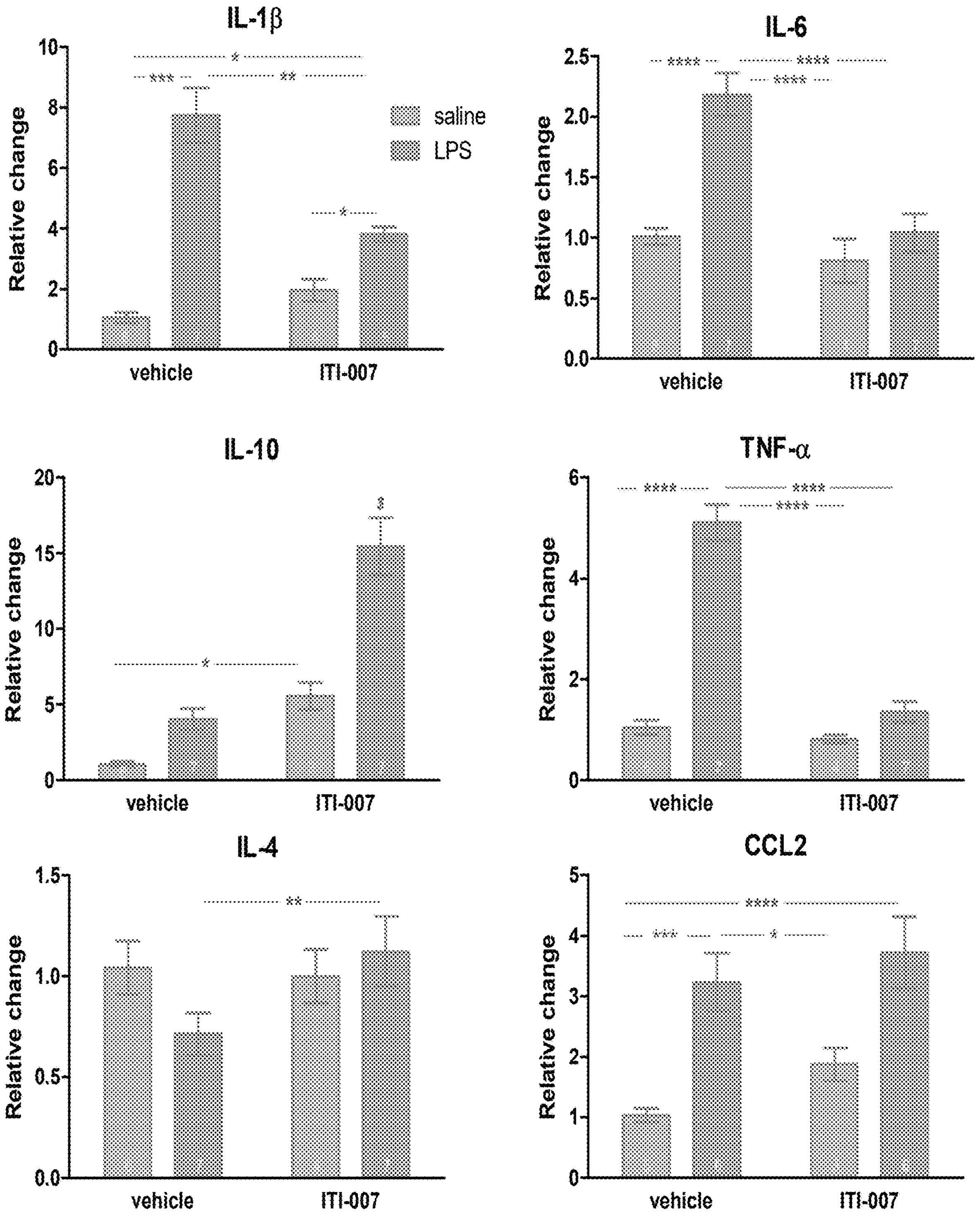
FIG. 10. Hippocampal pro- and anti-inflammatory cytokine expression measured by qPCR after mice were injected with LPS followed by test compound after 30 minutes.

The above experiment is repeated with a 30-minute delay between injection of LPS/saline and injection of ITI-007/vehicle and using only a single dose of ITI-007 (3.0 mg/kg). The results are shown in FIG. 10, normalized to the control group. The results demonstrate that lumateperone suppresses inflammatory cytokine production, even when administrated with a delay after LPS exposure.

Restraint Stress Experiment

Male, C57/B16 mice (n=6-7/group) are divided into three groups-control (vehicle alone, no stress), vehicle-stress (vehicle, i.p.), or ITI-007-stress (3 mg/kg, i.p. in vehicle). For induction of stress, mice are placed in a plastic "decapicones" and placed on the bottom of a warm, clean rodent cage for a 2 h period. These plastic "decapicones" produce an acute restraint stress which triggers neuroinflammation in both hippocampal tissue and peripherally (as shown by serum). At the end of the stress exposure, mice are killed; blood is taken for serum preparation and brain tissue for analysis. Serum is prepared from blood; cytokine measures are performed using MSD multiplex analysis. Brain tissue is analyzed by qPCR for pro-inflammatory cytokine mRNA expression.

Figure 2:
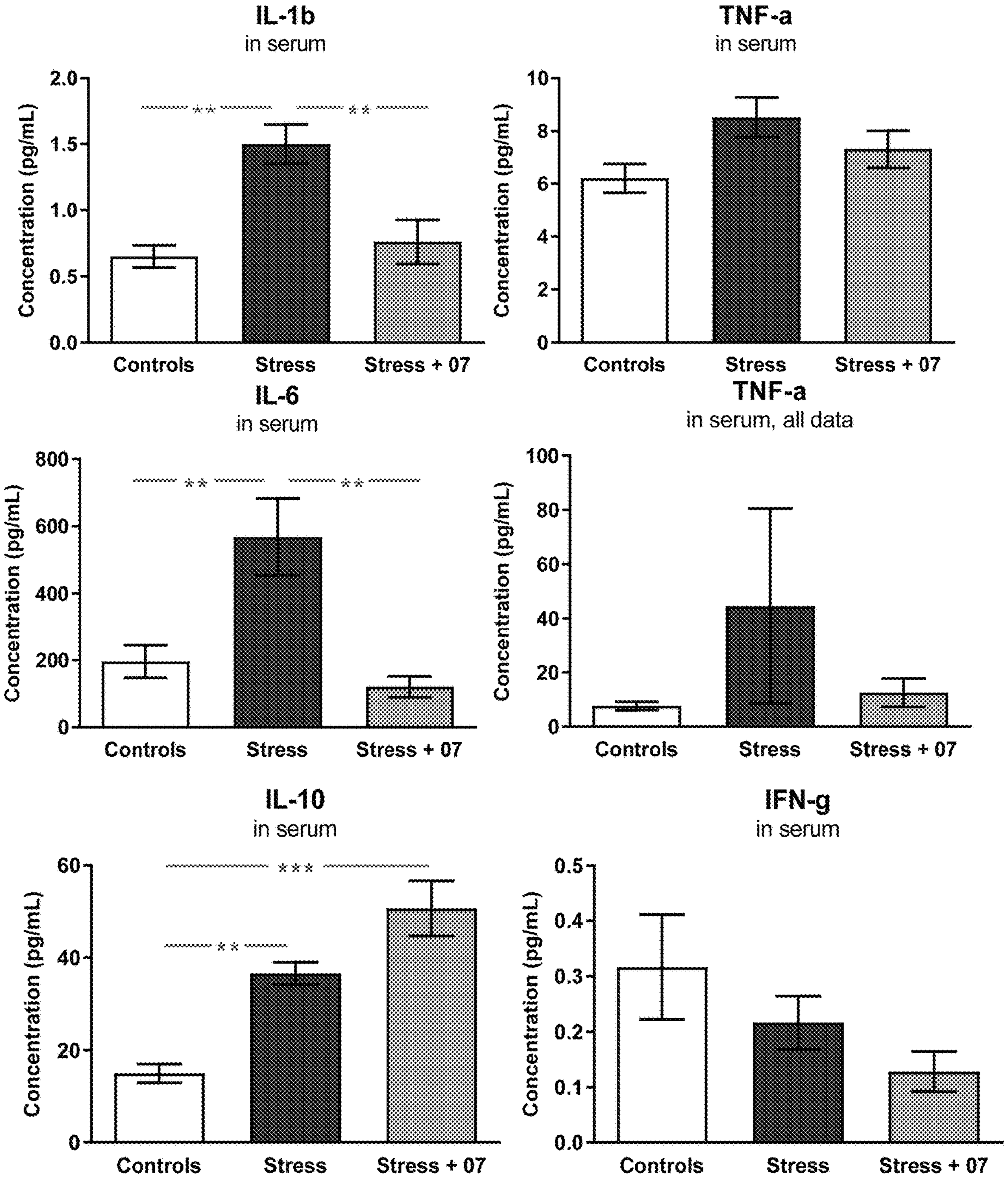
FIG. 2. Pro- and anti-inflammatory cytokine concentration measured in blood serum after mice were subjected to restraint stress.

As seen in FIG. 1, while there are trends, there are not statistically significant effects on hippocampal expression of pro-inflammatory cytokines by qPCR in response to 2 h restraint stress, although such cytokine expression is generally depressed by restraint stress plus lumateperone. CCL2 and IL-10 levels, as an exception however, are elevated in response to stress plus lumateperone (not statistically significant). As seen in FIG. 2, stress exposure significantly elevated serum IL-1β and IL-6 levels ($p<0.01$ vs Control, ANOVA). Levels of TNF, IL-10, and IFN-gamma are not significantly affected by this stress paradigm. Pre-treatment with lumateperone (ITI-007) (3 mg/kg, i.p.) significantly attenuates stress effects on IL-1β and IL-6 ($p<0.01$ vs ANOVA); effects on TNF and IL-10 are trends, but not statistically significant.

Exposure of mice to an acute stressor (i.e., restraint stress) robustly elevates circulating levels of pro-inflammatory cytokines detected in plasma, including IL-1β and IL-6.

Administration of lumateperone (3 mg/kg, i.p.), just prior to the induction of stress, thus significantly attenuates stress-induced serum cytokine levels. Hippocampal cytokine expression is not reliably changed in this experiment, when measured immediately after stress exposure. These data support our previous observations that lumateperone suppresses LPS-induced expression of pro-inflammatory cytokines in mouse brain by demonstrating an anti-inflammatory effect of lumateperone administration in response to a physiological stressor.

Effects on mTOR Signaling

It is known that upstream and downstream effectors of the mTOR (e.g., mTORC1) signaling pathway are increased in the mPFC of rats 1 hour and 24 hours after administration of the rapid-acting antidepressant ketamine. We use ketamine as a positive control and compare it to the potential effects of lumateperone on the same signaling pathway. In this study, lumateperone is given at different doses ranging from 1 to 8 mg/kg (i.p.) to adult rats and brain samples are analyzed 60 min, 90 min or 24 hours later. Results show that, like ketamine (30 mg/kg), lumateperone rapidly activates the mTORC1 signaling pathway in mPFC, and particularly in those intracellular cascades involved in synaptic plasticity (i.e., p-Akt thr308 and p-P70S6K). More precisely, lumateperone has a longer lasting effect compared with ketamine (30 mg/kg) on phospho-protein levels at 24 hours, which is consistent with the longer-lasting pharmacokinetic profile of lumateperone in vivo.

As seen in FIG. 3, lumateperone is unusual among antipsychotic drugs in possessing very high SERT inhibition. IC200131, which is the compound according to Formula I, wherein X is $N(CH_3)$, and Y is CH(OH), also shows high SERT inhibition.

Lumateperone, given alone, uniquely enhances both NMDA and AMPA receptor currents in mPFC neurons via activation of D1 receptors. Lumateperone (ITI-007), alone, in a bath applied to rat mPFC slices (3-100 nM) enhanced NMDA and AMPA currents 5 min later measured using intracellular whole-cell patch clamp techniques (Björkholm et al., 2015). The effect of lumateperone (30 nM) (*$p<0.05$; **$p<0.01$, t-test) is fully blocked in the presence of the D1 receptor antagonist, SCH-23390 (1 μM) (*$p<0.05$; **$p<0.01$; ##, $p<0.01$, t-test). Combined administration of the antipsychotic, olanzapine, and the SSRI, fluoxetine, similarly induces rapid antidepressant activity in humans and animals (Tohen et al., 2010); likewise, combined application of olanzapine and fluoxetine is required to induce AMPA receptor currents in vitro.

Figure 4:
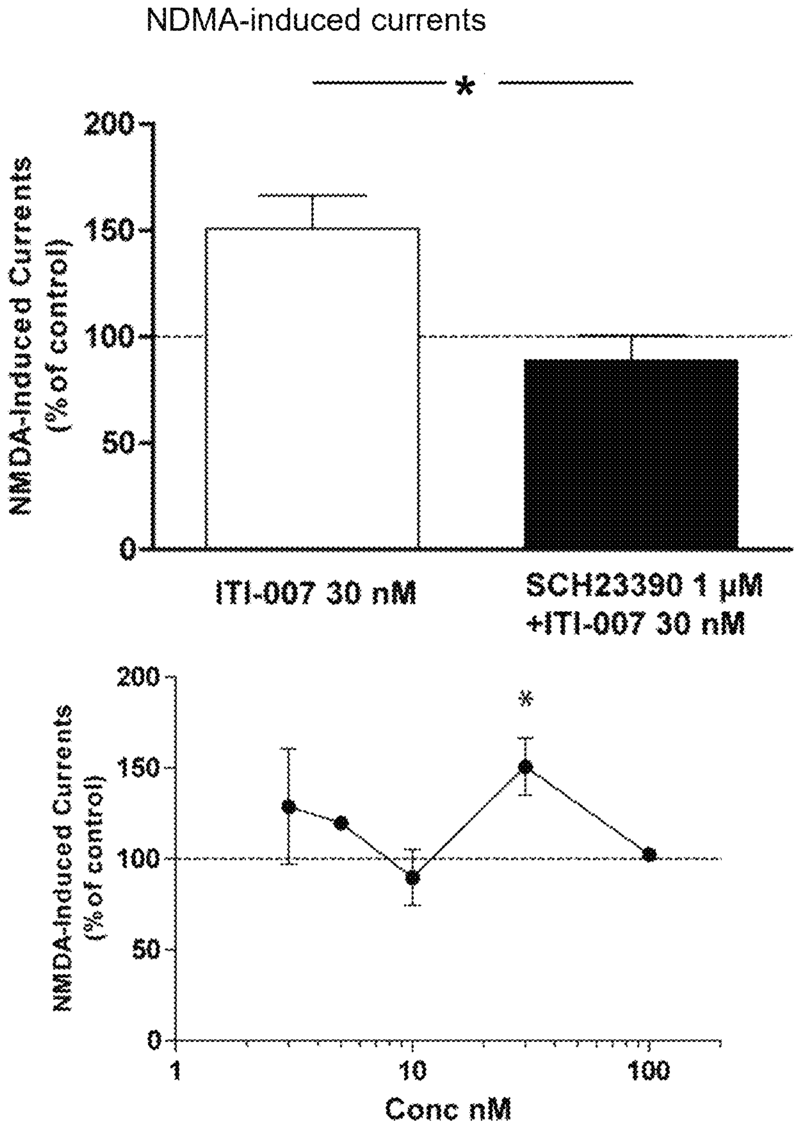
FIG. 4. Enhancement of NMDA currents in rat pre-frontal cortex via activation of D1 receptors.
Figure 5:
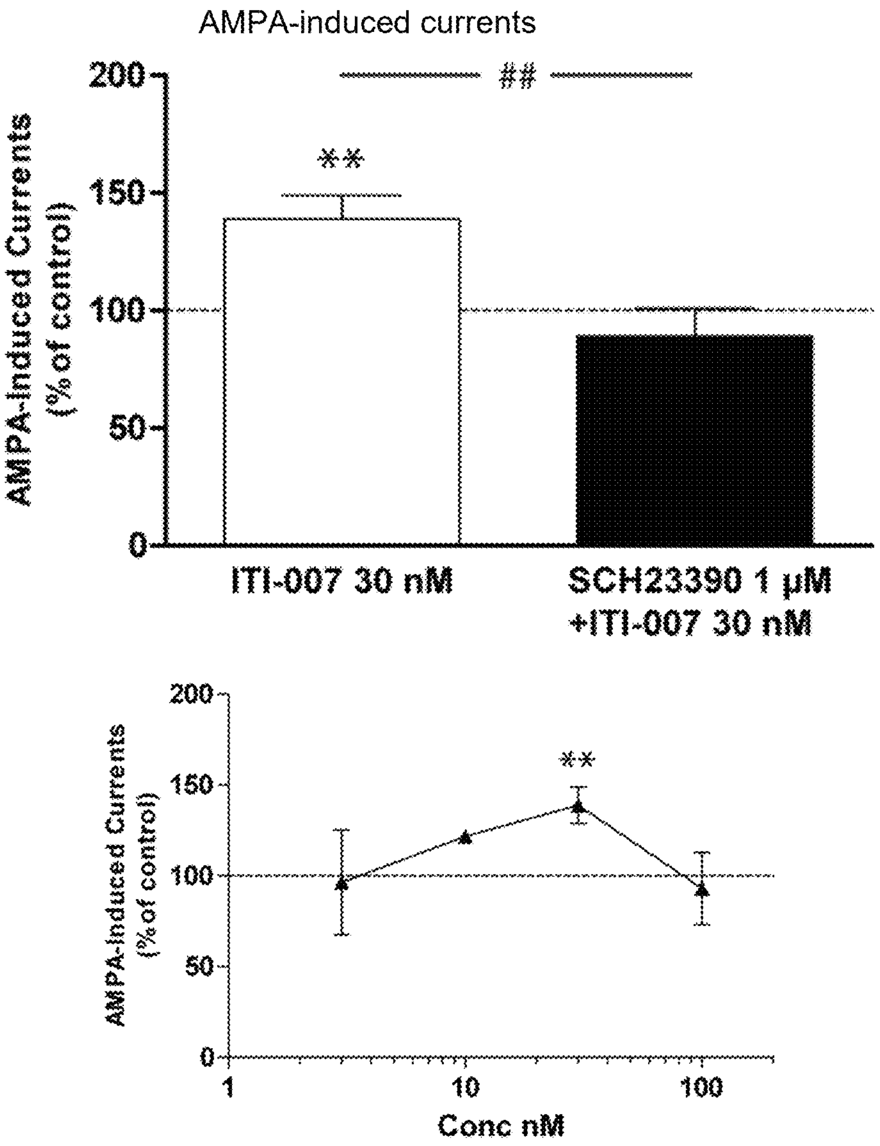
FIG. 5. Enhancement of AMPA currents in rat pre-frontal cortex via activation of D1 receptors.
Figure 6:
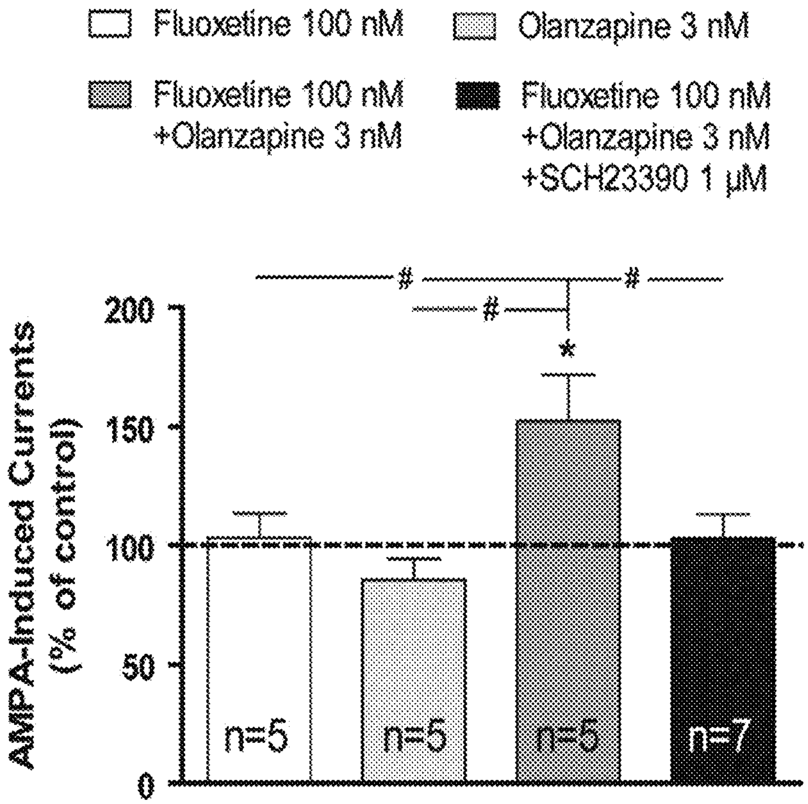
FIG. 6. Enhancement of AMPA currents in rat pre-frontal cortex by combination of olanzapine and fluoxetine.

FIGS. 4 and 5 show that lumateperone alone enhances NMDA- and AMPA-induced currents, while FIG. 6 shows that another antipsychotic drug, olanzapine, enhances AMPA-induced currents only in the presence of the SSRI, fluoxetine.

Figure 7:
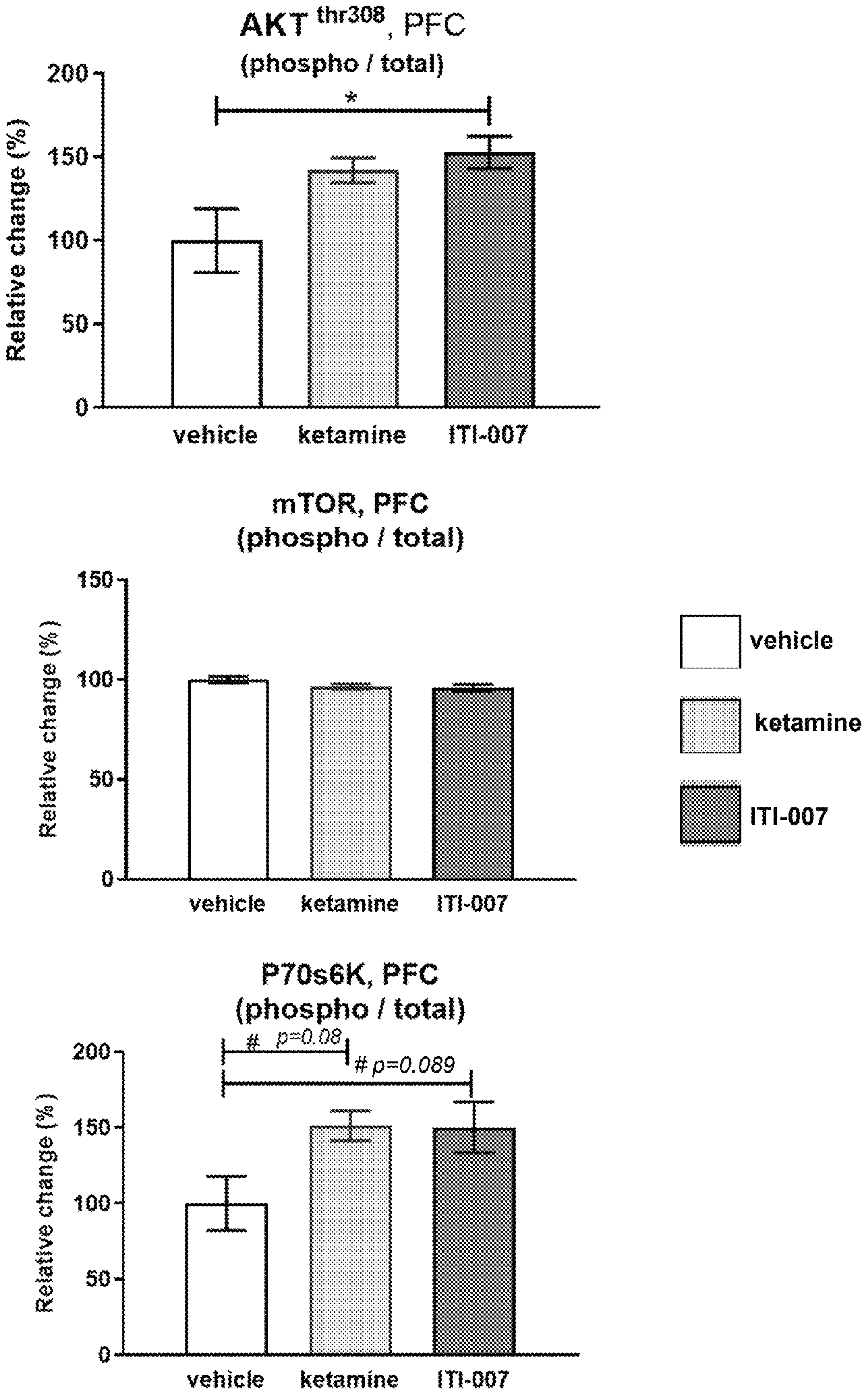
FIG. 7. Changes in mTOR signaling pathway phosphoprotein expression in rat prefrontal cortex after administration of lumateperone or ketamine (shown by relative change).
Figure 8:
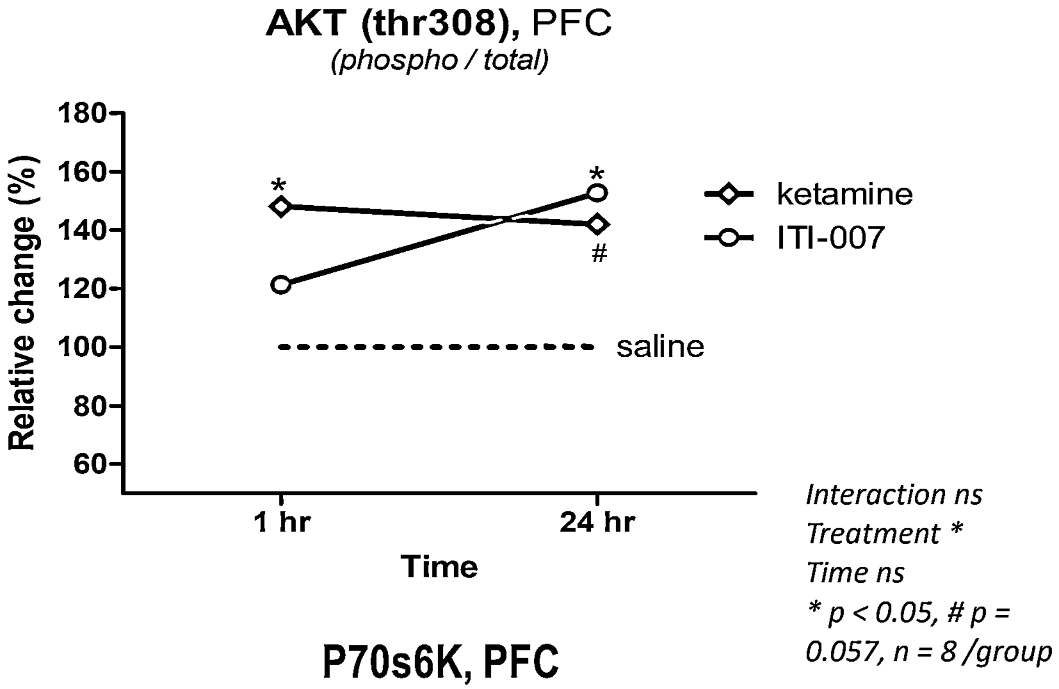
FIG. 8. Changes in mTOR signaling pathway phosphoprotein expression in rat prefrontal cortex after administration of lumateperone or ketamine (shown by time course of change).
Figure 8:
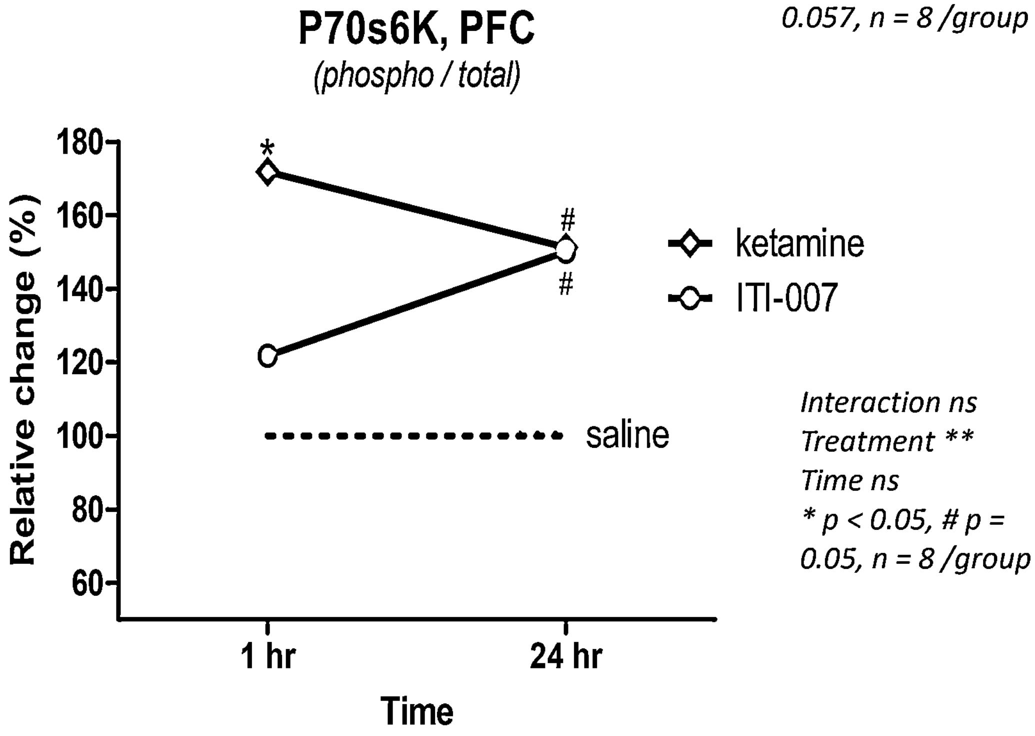

FIG. 7 shows the effects of lumateperone (ITI-007) and ketamine on the phosphorylation of mTOR pathway proteins in rat PFC at 24 hours post-administration. In this experiment, rats (N=8/group) are treated with one intraperitoneal injection (acutely) with either 30 mg/kg ketamine, or 3 mg/kg lumateperone (ITI-007) in a vehicle of: 5% DMSO, 5% Tween20, 15% PEG400 and 75% water, and sacrificed 24 h later. Pre-frontal cortical phosphorylation levels of AKT (at Threonine 308), mTOR (at Serine 2448) or P70s6 kinase (at Threonine 389) are evaluated after normalization to total protein levels for each target, at both 1 hour and 24 hours. Results are shown as the percent relative change compared to placebo (saline). It is found that both lumateperone and ketamine increase phosphorylation of AKT at thr308 at both 1 hour and 24 hours post-administration. The effect shown for lumateperone is both stronger at 24 hours than for ketamine, and is not declining in intensity, as shown in FIG. 8. Neither ketamine nor lumateperone results in a change in mTOR phosphorylation. Ketamine is found to transiently increase p70s6K phosphorylation, an effect which attenuates over the 24 time period, whereas lumateperone progressively increases p7-s6K phosphorylation over the 24 hour period. Overall, these results show that lumateperone alters the mTORC1 signaling pathways in the same way as ketamine, but with more prolonged effects.

Lumateperone thus enhances both NMDA and AMPA-induced currents in mPFC pyramidal neurons via activation of D1 receptors. These changes have been implicated in the mechanism of action of rapid-acting antidepressants. Lumateperone alone activates AMPA-type receptor currents in mPFC in a manner previously reported only after combined application of an antipsychotic drug (e.g., olanzapine, asenapine, brexpiprazole, or risperidone) and a selective serotonin reuptake inhibitor (SSRI; fluoxetine or citalopram), or after ketamine, which also exhibits rapid onset antidepressant activity in humans.

Additionally, lumateperone, like ketamine, increases protein phosphorylation of key proteins in the mTOR pathway, including the protein kinase, Akt, and p70S6 kinase, further supporting activation of a common pathway by lumateperone and ketamine. Clinically, combined adjunctive treatment with a low-dose of APD (e.g., olanzapine, quetiapine, or aripiprazole), and an SSRI, like fluoxetine, induces rapid, sustained antidepressant effects in patients with TRD. These data support that lumateperone achieves enhanced glutamatergic neurotransmission, owing to multiple pharmacological properties, including its uniquely potent activity (among antipsychotic medications) as a SERT inhibitor and its ability to enhance dopamine neurotransmission via D1 receptors. Lumateperone and its alcohol metabolite (IC200131) each elicit antidepressant-like behaviors in rodents. Lumateperone is safe and well-tolerated in humans. Lumateperone improves symptoms of depression in patients with schizophrenia and is currently in Phase III clinical trials in patients with bipolar depression. Lumateperone is also in Phase III development for the treatment of schizophrenia and for agitation associated with dementia, including Alzheimer's Disease.

Together these studies further elucidate the signaling pathways that underlie lumateperone administration, supporting a fast-acting antidepressant action via indirect dopamine D1 receptor-dependent enhancement of NMDA and AMPA currents coupled with activation of the mTORC1 signaling pathway, and paralleled by anti-inflammatory properties. Based on these data, lumateperone may be useful as a single, stand-alone, orally-available, rapid-acting treatment for depression and anxiety, lacking the adverse side effects of ketamine and other current pharmacological approaches.

Example 2: Lumateperone Down-Regulates Genes Involved in Inflammation and Microglia Activation and Upregulates Genes Involved in Neuroprotection and Growth Factor Signaling Adult mice are injected intraperitoneally with either lumateperone tosylate (at 3 mg/kg in vehicle or with vehicle alone (vehicle is 5% DMSO, 5% Tween 20, 15% PEG-400 and 75% water). Immediately after this injection, the mice are injected with either LPS (500 μg/kg diluted in 0.9% saline) or with 0.9% saline. After 2 hours, the mice are sacrificed, and hippocampal mRNA is obtained, as described in Example 1.

Hippocampal RNA concentration and integrity are evaluated using an Agilent 2100 Bioanalyzer. Sample preparation, hybridization and detection are carried out according to NanoString manufacturer's instructions (NanoString technologies, WA). RNA (100 ng) expression profiling is performed using the nCounter NanoString Mouse Neuropathology panel, and data are analyzed using the nSolver software to produce and compare direct counts of mRNA. NanoString results (raw and normalized counts) are derived from RCC files using the nSolver software (version 2.6). The neuropathology panel was developed to include genes of relevance for research in models of neurodegenerative and neurological disorders, such as Alzheimer's disease, Parkinson's disease, Amyotrophic Lateral Sclerosis, Frontotemporal Dementia, and Huntington's disease. The panel includes 770 genes associated with themes of neurotransmission, neuron-glia interaction, neuroplasticity, cell structure integrity, neuroinflammation and metabolism.

The results are shown in the table below:

Genes Up-Regulated in Mice Treated with Lumateperone/LPS Compared to vehicle/LPS

| Genes | Linear Change | Associated Pathways |
|---|---|---|
| Cldn5 | >1.5 fold | Tissue integrity |
| Egr1, Gata2, Olig2, | 1.25-1.5 fold | Growth factor signaling, angiogenesis, chromatin modification, myelination |
| Phf21a, Islr2, Ngf, Arrb2, Homer1, Notch1, Rapgef2, | 1.1-1.25 fold | Tissue integrity, growth factor signaling, chromatin modification, angiogenesis, axon and dendrite structure, trophic factors, transmitter |

-continued

| Genes Up-Regulated in Mice Treated with Lumateperone/LPS Compared to vehicle/LPS | | |
|---|---|---|
| Genes | Linear Change | Associated Pathways |
| Pde4d | | response and uptake |
| Syt4, Adcy9, Gabrb2, Slc8a1, Inppf5, Scn1a, Pten, Crebbp | 1.0-1.1 fold | Neural connectivity, vesicle trafficking, growth factor signaling, chromatin modification, angiogenesis, axon and dendrite structure, transmitter response and uptake |
| Hc, Osmr | <0.500-fold | Angiogenesis, cytokines, disease association |
| Ptgs2, Cp, Cntf, Tnfrsf1a, Il1R1 | 0.5-0.75-fold | Activated microglia, angiogenesis, disease association, growth factor signaling, cytokines, apoptosis |
| Nfe2l2, Naglu, Pla2g4b, Npas4, Nos3 | 0.75-0.80-fold | Oxidative stress, activated microglia, autophagy, growth factor signaling, neural connectivity, angiogenesis |
| Ctns, Jun, Polr2l, Usp21, Csf1, Sirt1, Atf4, Fclrls | 0.80-0.85 fold | Oxidative stress, activated microglia, autophagy, angiogenesis, apoptosis, transcription and splicing, disease association, chromatin modification, cytokines |

These results suggest that lumateperone enhances expression of genes that maintain tissue integrity and promote proper structure and function of neurons in the brain in animals receiving an inflammatory challenge (here, LPS). In fact, one of the genes most highly enhanced by lumateperone is that for claudin-5 (Cldn5), an endothelial tight junction protein with a role in maintaining the integrity of the blood-brain-barrier. Expression of Cldn5 has previously been shown to protect the brains of mice from neurovascular pathology induced by chronic social stress (Menard et al., 2017). In addition, treatment of LPS-challenged mice with lumateperone significantly suppressed the expression of genes that promote oxidative stress, apoptosis and autophagy. Together, the data support a role for lumateperone as a neuroprotective agent.

We claim:

1. A method of treating acute depression and/or acute anxiety, comprising administering to a patient in need thereof, a therapeutically effective amount of a Compound of Formula I:

Formula I

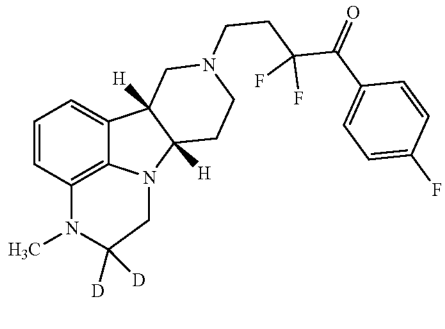

in free, or in pharmaceutically acceptable salt-form; wherein D represents a hydrogen position with greater than 90% deuterium incorporation; wherein the acute anxiety is selected from a short-duration anxious episode associated with generalized anxiety disorder, panic disorder, specific phobias, or social anxiety disorder, or social avoidance, and wherein the acute depression is selected from an acute major depressive episode, an acute short-duration depressive episode, and an acute recurrent brief depressive episode;

wherein the method comprises once daily administration of a unit dosage for transmucosal administration, comprising the compound of Formula I in tosylate salt form in an amount equivalent to 0.5 to 30 mg of free base, and a pharmaceutically acceptable diluent or carrier, wherein the unit dosage for transmucosal administration is a sublingual or buccal orally disintegrating tablet.

2. The method according to claim 1, wherein the condition to be treated is acute anxiety, wherein the acute anxiety is selected from a short-duration anxious episode associated with generalized anxiety disorder, panic disorder, specific phobias, or social anxiety disorder, or social avoidance.

3. The method according to claim 1, wherein the condition to be treated is acute depression, wherein the acute depression is selected from an acute major depressive episode, an acute short-duration depressive episode, and an acute recurrent brief depressive episode.

4. The method according to claim 1, wherein the therapeutically effective amount of the Compound of Formula I is sufficient to enhance mTOR signaling.

5. The method according to claim 1, wherein the therapeutically effective amount of the Compound of Formula I is sufficient to reduce neuroinflammation.

6. The method according to claim 1, wherein the unit dosage for transmucosal administration is a buccal orally disintegrating tablet.

7. The method according to claim 1, wherein the method further comprises the concurrent administration of an NMDA receptor antagonist.

8. The method according to claim 1, wherein the method further comprises the concurrent administration of a NMDA receptor allosteric modulator.

9. The method according to claim 1, wherein the method provides the patient with an acute response to treatment with the Compound of Formula I.

10. The method according to claim 1, wherein the patient has not responded to, or has not responded adequately to, or who suffers undesirable side effects from, treatment with another antidepressant agent.

11. The method according to claim 1, wherein the Compound of Formula I is administered as monotherapy.

12. The method according to claim 1, wherein the method does not put the patient at risk for sedation, dissociation, abuse, misuse, or suicidal ideation, or does not result in hypertension within four hours after administration of a dose of the compound of Formula I.

13. The method according to claim 2, wherein the acute anxiety is a short-duration anxious episode associated with generalized anxiety disorder.

14. The method according to claim 3, wherein the acute depression is an acute major depressive episode.

15. The method according to claim 3, wherein the acute depression is alleviated within one week of treatment.

16. The method according to claim 3, wherein the patient shows an acute response to treatment within less than 2 weeks of treatment.

17. The method according to claim 2, wherein the acute anxiety is alleviated within one week of treatment.

18. The method according to claim 2, wherein the patient shows an acute response to treatment within less than 2 weeks of treatment.

19. The method according to claim 1, wherein D represents a hydrogen position with greater than 97% deuterium incorporation.

20. The method according to claim 1, wherein the unit dosage for transmucosal administration is a sublingual orally disintegrating tablet.

21. The method according to claim 10, wherein the antidepressant agent is selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor, or a serotonin receptor antagonist).

22. The method according to claim 14, wherein the acute major depressive episode is associated with bipolar disorder or major depressive disorder.

23. The method according to claim 1, wherein the unit dosage for transmucosal administration comprises the compound of Formula I in tosylate salt form in an amount equivalent to 1 to 10 mg of free base.

24. The method according to claim 1, wherein the patient is under concurrent treatment with an oral antidepressant selected from duloxetine, escitalopram, sertraline, or venlafaxine.

25. The method according to claim 1, wherein the method further comprises the concurrent administration of another antidepressant agent.

26. The method according to claim 25, wherein the other antidepressant agent is selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof.

27. The method according to claim 26, wherein the other antidepressant agent is selected from citalopram, escitalopram, paroxetine, fluoxetine, fluvoxamine, sertraline, desvenlafaxine, duloxetine, levomilnacipran, milnacipran, tofenacin, venlafaxine, amitriptyline, amitriptylinexide, clomipramine, desipramine, dibenzepin, dimetacrine, dosulepin, doxepin, imipramine, lofepramine, melitracen, nitroxazepine, nortriptyline, noxiptiline, pipofezine, protriptyline, and trimipramine, or any combination thereof.

* * * * *